United States Patent
Cooymans et al.

(10) Patent No.: US 8,865,705 B2
(45) Date of Patent: Oct. 21, 2014

(54) BENZIMIDAZOLE RESPIRATORY SYNCYTIAL VIRUS INHIBITORS

(75) Inventors: Ludwig Paul Cooymans, Beerse (BE); Samuël Dominique Demin, Antwerp (BE); Lili Hu, Mechelen (BE); Tim Hugo Maria Jonckers, Edegem (BE); Pierre Jean-Marie Bernard Raboisson, Rosieres (BE); Abdellah Tahri, Anderlecht (BE); Sandrine Marie Helene Vendeville, Woluwe-Saint-Pierre (BE)

(73) Assignee: Janssen R&D Ireland (IE)

( * ) Notice: Subject to any disclaimer, the term of this patent is extended or adjusted under 35 U.S.C. 154(b) by 0 days.

(21) Appl. No.: 13/993,107

(22) PCT Filed: Dec. 16, 2011

(86) PCT No.: PCT/EP2011/073008
§ 371 (c)(1),
(2), (4) Date: Jun. 11, 2013

(87) PCT Pub. No.: WO2012/080446
PCT Pub. Date: Jun. 21, 2012

(65) Prior Publication Data
US 2013/0267508 A1    Oct. 10, 2013

(30) Foreign Application Priority Data
Dec. 16, 2010    (EP) .................................... 10195467

(51) Int. Cl.
*C07D 471/04*    (2006.01)

(52) U.S. Cl.
USPC ............... 514/222.2; 514/303; 514/234.2; 546/118; 544/127; 544/3

(58) Field of Classification Search
USPC .............. 546/118; 514/222.2, 303, 234.2; 544/127, 3
See application file for complete search history.

(56) References Cited

U.S. PATENT DOCUMENTS

| 6,489,338 B2 * | 12/2002 | Yu et al. ........................ 514/303 |
| 6,506,738 B1 | 1/2003 | Yu et al. |
| 6,534,535 B1 | 3/2003 | Zhu et al. |
| 6,919,331 B2 * | 7/2005 | Yu et al. ...................... 514/223.2 |
| 7,361,657 B2 | 4/2008 | Janssens et al. |
| 7,528,149 B2 | 5/2009 | Janssens et al. |
| 2002/0016309 A1 | 2/2002 | Yu et al. |
| 2004/0166137 A1 | 8/2004 | Lackey |
| 2013/0261151 A1 | 10/2013 | Cooymans et al. |
| 2013/0267508 A1 | 10/2013 | Cooymans et al. |
| 2013/0267555 A1 | 10/2013 | Cooymans et al. |
| 2013/0267556 A1 | 10/2013 | Cooymans et al. |
| 2013/0324527 A1 | 12/2013 | Cooymans et al. |

FOREIGN PATENT DOCUMENTS

| WO | 98/01428 | 1/1998 |
| WO | 00/20400 | 4/2000 |
| WO | 01/95910 | 12/2001 |
| WO | 02/26228 | 4/2002 |
| WO | 03/053344 | 4/2003 |

OTHER PUBLICATIONS

Pearce et al., J. Chem. Inf. Model. (2009), 49, pp. 1797-1809.*
Wang et al., Bioorganic & Medicinal Chemistry Letters (2007), 17(16), 4592-4598.*
International Search Report—PCT/EP2011/073008, dated, Mar. 28, 2012.
International Search Report—PCT/EP2011/073011, dated, Mar. 27, 2012.
International Search Report—PCT/EP2011/073014, dated Mar. 28, 2012.
International Search Report—PCT/EP2011/073016, dated, Mar. 27, 2012.
International Search Report—PCT/EP2011/073017, dated Mar. 28, 2012.
Banker, et al., Modern Pharmaceutics, 3 edition, 1996, pp. 451 and 596.
Wang, et al., "Respiratory Syncytial virus Fusion Inhibitors. Part 5: Optimization of Benzimidazole Substitution Patterns Towards Derivatives with Improved Activity", Biorganic and Medicinal Chemistry Letters, vol. 17, 2007, pp. 4592-4598.
Beaulieu, et al., "Improved Replicon Cellular Activity of Non-Nucleoside Allosteric Inhibitors of HCV NS5B Polymerase: From Benzimidazole to Indole Scaffolds", Biorganic & Medicinal Chemistry letters 16, 2006, pp. 4987-4993.
Goodman, et al, Biotransformation of Drugs:, The Pharmacological Basis of Therapeutics, $8^{th}$ ed., 1992, pp. 13-15.
Giampieri, et al., "Antiviral Activity of Indole Derivatives", Antiviral Research, vol. 83, 2009, pp. 179-185.
Wyde, et al., AWY Dentiviral Research, vol. 38, 1998, pp. 31-42.
Wolff, et al., "Burger's Medicinal Chemistry, $5^{th}$ edition", Part I, pp. 975-977.
Wermuth, "Molecular Variations Based on Isosteric Replacements", Practice of Medicinal Chemistry $3^{rd}$ edition, 2008, pp. 290-342.

(Continued)

*Primary Examiner* — Niloofar Rahmani
(74) *Attorney, Agent, or Firm* — Mary A. Appollina

(57) ABSTRACT

Benzimidazoles having inhibitory activity on RSV replication and having the formula formula (I)

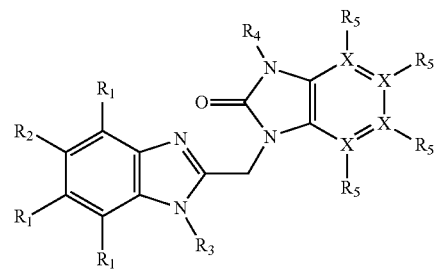

the prodrugs, N-oxides, addition salts, quaternary amines, metal complexes and stereochemically isomeric forms thereof, compositions containing these compounds as active ingredient and processes for preparing these compounds and compositions.

16 Claims, No Drawings

(56) References Cited

OTHER PUBLICATIONS

Yu, et al., "Respiratory Syncytial Virus Fusion Inhibitors. Part 4: Optimization for Oral Bioavailability" Biorganic & Medicinal Chemistry letters, vol. 17, 2007, pp. 895-901.

Silverman, et al., The Organic of Drug Design and Drug Action, pp. 29-34.

Pearce, et al., "E-Novo: An Automated Workflow for efficient Structure-Based Lead Optimization" J. Chem. Inf. Model, 2009, vol. 49, pp. 1797-1809.

Ito, et al., "A Medium-Term Rat Liver Bioassay for Rapid in Vivo Detection of Carcinogenic Potential of Chemicals" Cancer Science, 94(1) 2003, pp. 3-8.

Database Registry Chemical Abstracts Service, Columbus, Ohio, Assession No. RN 941045-14-3 and RN 931665-23-5.Entered STN: Jul. 4, 2007 and Apr. 22, 2007.

* cited by examiner

BENZIMIDAZOLE RESPIRATORY SYNCYTIAL VIRUS INHIBITORS

CROSS REFERENCE TO RELATED APPLICATIONS

This application is the national stage under 35 U.S.C. 371 of PCT Application No. PCT/EP2011/073008, filed Dec. 16, 2011, which application claims priority from European Patent Application No. EP 10195467.5, filed Dec. 16, 2010, the entire disclosures of which are hereby incorporated by reference in their entirety.

FIELD OF THE INVENTION

The invention concerns benzimidazoles having antiviral activity, in particular, having an inhibitory activity on the replication of the respiratory syncytial virus (RSV). The invention further concerns the preparation of these benzimidazoles, compositions comprising these compounds, and the compounds for use in the treatment of respiratory syncytial virus infection.

BACKGROUND

Human RSV or Respiratory Syncytial Virus is a large RNA virus, member of the family of Paramyxoviridae, subfamily pneumoviridae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue, which provides an aerosol treatment for serious RSV infection in hospitalized children. The aerosol route of administration, the toxicity (risk of teratogenicity), the cost and the highly variable efficacy limit its use. The other two drugs, RespiGam® (RSV-IG) and Synagis® (palivizumab), polyclonal and monoclonal antibody immunostimulants, are intended to be used in a preventive way. Both are very expensive, and require parenteral administration.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication. It would be particularly preferred to provide drugs against RSV replication that could be administered perorally.

A reference on benzimidazole antiviral agents is WO 01/95910. Herein compounds are presented to have antiviral activity, yet with $EC_{50}$ values over a wide range of from 0.001 µm to as high as 50 µM (which does not normally represent the desired biological activity). Another reference, relating to substituted 2-methyl-benzimidazole RSV antiviral agents, in the same range of activities is WO 03/053344. Another related background reference on compounds in the same range of activities, is WO 02/26228 regarding benzimidazolone antiviral agents. A reference on structure-activity relations, in respect of RSV inhibition, of 5-substituted benzimidazole compounds is X. A. Wang et al., Bioorganic and Medicinal Chemistry Letters 17 (2007) 4592-4598.

It is desired to provide new drugs that have antiviral activity. Particularly, it would be desired to provide new drugs that have RSV replication inhibitory activity. Further, it would be desired to unravel compound structures that allow obtaining higher antiviral biological activities than disclosed in the art, and particularly having activities represented by $EC_{50}$ values below 0.001 µM. A further desire is to find compounds having oral antiviral activity.

SUMMARY OF THE INVENTION

In order to better address one or more of the foregoing desires, the invention, in one aspect, presents antiviral benzimidazole compounds represented by formula I, a prodrug, N-oxide, addition salt, quaternary amine, metal complex, or a stereochemically isomeric form thereof;

formula (I)

wherein
each X independently is C or N;
$R_1$ is H;
$R_2$ is selected from the group consisting of Br and Cl;
$R_3$ is —$(CR_6R_7)_n$—$R_8$;
$R_4$ is selected from the group consisting of H, $C_3$-$C_7$cycloalkyl, $C_2$-$C_{10}$ alkenyl, —$(CR_6R_7)_n$—$R_8$, —$CH_2$-p-Fluorophenyl, $CH_2CF_3$ and —$SO_2CH_3$;
$R_5$ is present where X is C, whereby each $R_5$ is selected, each independently, from the group consisting of H, $C_1$-$C_6$alkyl, $C_1$-$C_6$alkoxy, halogen, and CN;
$R_5$ is absent where X is N;
$R_6$ and $R_7$ are each independently chosen from H and $C_1$-$C_{10}$ alkyl, $C_3$-$C_7$cycloalkyl; or
$R_6$ and $R_7$ taken together form a 5 to 6 membered aliphatic or aromatic ring that optionally contains one or more heteroatoms selected from the group N, S, O.
$R_8$ is selected from the group consisting of H, OH, $CF_3$, $CHF_2$, F, Cl, $SO_2CH_3$, $SO_2C_3$-$C_7$cycloalkyl, $NR_6SO_2R_6$, $SO_2NR_6R_7$, $NR_6SO_2C_3$-$C_7$cycloalkyl, CN, $NR_6R_7$, COOH, $COOR_6$, $CONR_6R_7$, $OCOC_1$-$C_6$alkyl, $CONR_6SO_2R_7$, $CONHR_6SO_2R_7$; $CONHR_6SO_2NR_6R_7CONR_6SO_2NR_6R_7$, phtalimido or a 5 to 6 membered aliphatic or aromatic ring that optionally contains one or more heteroatoms selected from the group N, S, O;
n is an integer having a value from 1 to 6;

In another embodiment,
each X independently is C or N;
$R_1$ is H;
$R_2$ is selected from the group consisting of Br and Cl;
$R_3$ is —$(CR_6R_7)_n$—$R_8$;
$R_4$ is selected from the group consisting of H, $C_3$-$C_7$cycloalkyl, $C_2$-$C_{10}$alkenyl, and —$SO_2CH_3$;
$R_5$ is present where X is C, whereby each $R_5$ is selected, each independently, from the group consisting of H, $C_1$-$C_6$alkyl, $C_1$-$C_6$alkoxy, halogen, and CN;
$R_5$ is absent where X is N;
$R_6$ and $R_7$ are each independently chosen from H and $C_1$-$C_{10}$ alkyl; or $R_6$ and $R_7$ taken together form a 5 to 6 membered aliphatic ring that optionally contains a heteroatom selected from the group N, S, O.
$R_8$ is selected from the group consisting of H, OH, $CF_3$, $CHF_2$, F, $SO_2CH_3$, $SO_2C_3$-$C_7$cycloalkyl, $NR_6SO_2R_6$, $SO_2NR_6R_7$, $NR_6SO_2C_3$-$C_7$cycloalkyl, CN, $NR_6R_7$, COOH, $COOR_6$, $CONR_6R_7$, $OCOC_1$-$C_6$alkyl;
n is an integer having a value from 2 to 6;

In another aspect, the invention relates to the foregoing compounds for use in the treatment of RSV infections in warm-blooded animals, preferably humans. In yet another aspect, the invention presents a method of treatment of viral RSV infections in a subject in need thereof, comprising administering to said subject an effective amount of a compound as defined above. In still another aspect, the invention resides in the use of a compound as defined above, for the manufacture of a medicament in the treatment of RSV infections.

In a further aspect, the invention relates to a pharmaceutical composition comprising a compound as defined above, and a pharmaceutically acceptable excipient.

In a still further aspect, the invention provides methods for preparing the compounds defined above.

DETAILED DESCRIPTION OF THE INVENTION

The invention is based on the unexpected finding that, on certain 5-substituted benzimidazole compounds, a specifically chlorine or bromine substituent $R_2$ provides compounds with unexpectedly strong biological activities against RSV. Even in a scientific presentation of structure activity (the Wang reference mentioned above), the judicious combination of the present invention does not surface. None of the results presented by Wang suggests biological activity outperforming the aforementioned range of 0.001 µM-50 µM.

The present invention will further be described with respect to particular embodiments and with reference to certain examples but the invention is not limited thereto but only by the claims. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

The term 'prodrug' as used throughout this text means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, 8th ed., a McGraw-Hill, Int. Ed. 1992, "Biotransformation of Drugs", p. 13-15) describing prodrugs generally, is hereby incorporated. Prodrugs are characterized by a good aqueous solubility and bioavailability, and are readily metabolized into the active inhibitors in vivo.

As used herein $C_1$-$C_6$alkyl as a group or part of a group defines straight or branched chain saturated hydrocarbon radicals having from 1 to 6 carbon atoms such as methyl, ethyl, propyl, 1-methylethyl, butyl, pentyl, hexyl, 2-methylbutyl and the like.

$C_1$-$C_{10}$alkyl as a group or part of a group defines straight or branched chain saturated hydrocarbon radicals having from 1 to 10 carbon atoms such as the groups defined for $C_1$-$C_6$alkyl and heptyl, octyl, nonyl, 2-methylhexyl, 2-methylheptyl, decyl, 2-methylnonyl, and the like;

The term '$C_2$-$C_{10}$alkenyl' used herein as a group or part of a group is meant to comprise straight or branched chain unsaturated hydrocarbon radicals having at least one double bond, and preferably having one double bond, and from 2 to 10 carbon atoms such as ethenyl, propenyl, buten-1-yl, buten-2-yl, penten-1-yl, penten-2-yl, hexen-1-yl, hexen-2-yl, hexen-3-yl, 2-methylbuten-1-yl, hepten-1-yl, hepten-2-yl, hepten-3-yl, hepten-4-yl, 2-methylhexen-1-yl, octen-1-yl, octen-2-yl, octen-3-yl, octen-4-yl, 2-methylhepten-1-yl, nonen-1-yl, nonen-2-yl, nonen-3-yl, nonen-4-yl, nonen-5-yl, 2-methylocten-1-yl, decen-1-yl, decen-2-yl, decen-3-yl, decen-4-yl, decen-5-yl, 2-methylnonen-1-yl, and the like;

The term —$(CR_6R_7)_n$ used herein defines n repetitions of the $CR_6R_7$ subgroup, wherein each of these subgroups is independently defined.

Whenever a $C_2$-$C_{10}$alkenyl group is linked to a heteroatom it preferably is linked via a saturated carbon atom.

$C_1$-$C_6$alkoxy, as a group or part of a group defines an O—$C_1$-$C_6$alkyl radical, wherein $C_1$-$C_6$alkyl has, independently, the meaning given above.

$C_3$-$C_7$cycloalkyl is generic to cyclopropyl, cyclobutyl, cyclopentyl, cyclohexyl or cycloheptyl.

The term halogen is generic to fluoro, chloro, bromo and iodo.

It should be noted that the radical positions on any molecular moiety used in the definitions may be anywhere on such moiety as long as it is chemically stable.

Radicals used in the definitions of the variables include all possible isomers unless otherwise indicated. For instance pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar term is meant to include the compounds of general formula (I), their prodrugs, N-oxides, addition salts, quaternary amines, metal complexes and stereochemically isomeric forms.

It will be appreciated that some of the compounds of formula (I) may contain one or more centers of chirality and exist as stereochemically isomeric forms.

The term "stereochemically isomeric forms" as used hereinbefore defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyl-tartaric acid, ditoluoyltartaric acid and camphorsulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butane-dioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates, which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complexating properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

Without detracting from the overall scope of the invention, certain embodiments are discussed in more detail below.

In some embodiments $R_2$ is Br. In other embodiments, $R_2$ is Cl. In the most preferred embodiments, $R_2$ is Br.

With reference to $R_3$ being —$(CR_6R_7)_n$—$R_8$ as defined above, in a preferred embodiment both $R_6$ and $R_7$ are H. By further preference, n is 2-4, and most preferably n is 3 or 4.

$R_8$ is preferably selected from the group consisting of H, OH, F, $CF_3$, CN, and $SO_2CH_3$.

$R_4$ is preferably selected from the group consisting of $C_3$-$C_7$cycloalkyl, $C_2$-$C_{10}$ alkenyl, $CH_2CF_3$ and —$SO_2CH_3$, more preferably $C_3$-$C_7$cycloalkyl, $C_2$-$C_{10}$ alkenyl, and —$SO_2CH_3$. More preferably, $R_4$ is $C_3$-$C_7$cycloalkyl or $CH_2CF_3$. Most preferably, $R_4$ is cyclopropyl or $CH_2CF_3$.

In a preferred embodiment, and more preferably in conjunction with the other preferred embodiments, one X is N, and the other X's are C. In a most preferred embodiment, the one X that is N, is the X in para position to N—R$_4$.

Preferably, at most, one R$_5$ is selected from the group consisting of C$_1$-C$_6$alkyl, C$_1$-C$_6$alkoxy, halogen, and CN. Most preferably, all R$_5$ are H.

In yet another preferred embodiment, R$_2$ is Cl; one X is N and the other X's are C, wherein the N is in para position to N—R$_4$, and R$_4$ is cyclopropyl or CH$_2$CF$_3$.

Preferred compounds are the compounds listed in tables 1 and 2 below. Most preferred are compounds P1, P2, P3, P4, P5, P6, P7, P8, P9, P10, P11, P12, P13, P14, P15, P16, P17, P22, P23, P24, P25, P26, and P27. More preferably, compounds are those denoted P1, P2, P3, P4, P6 and P24. Most preferred compounds are those denoted P1, P2, P3, and P4.

The compounds of formula (I) can be synthesized for instance using one of the methods shown in Scheme 1. In general, a fragment A or B is coupled with a fragment C resulting in derivatives of formula (I).

Scheme 1. General synthesis of compounds of formula (I)

Method 1

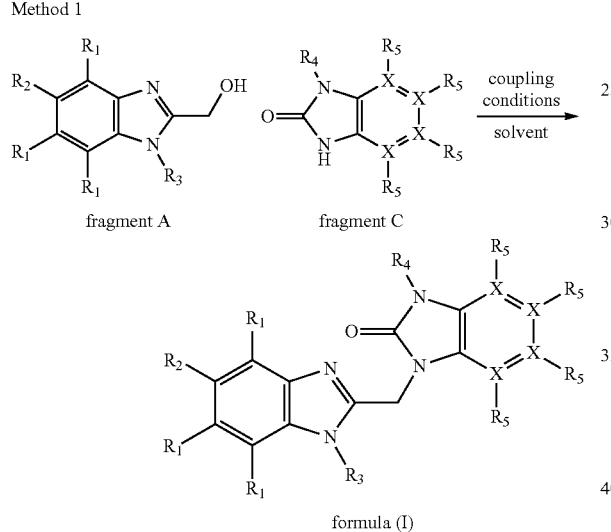

Method 2

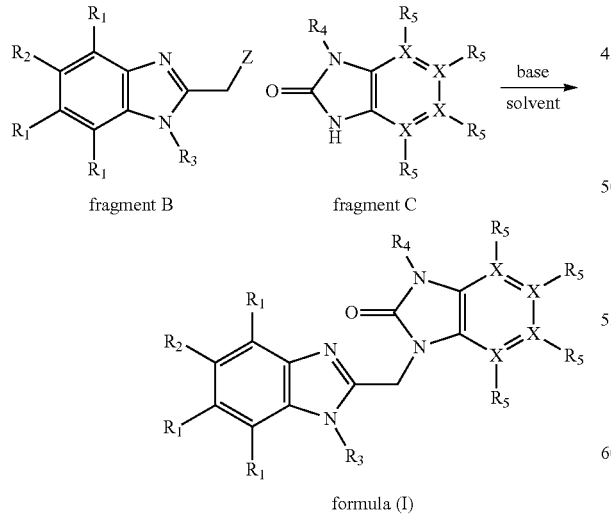

Z = Cl, Br, OTos, OMs

For method 1, an example of suitable "coupling conditions" to react a fragment A with a fragment C to form formula (I) type compounds is a Mitsunobu reaction. A suitable solvent for this type of reaction is THF (tetrahydrofuran).

Alternatively (but not limited to), a fragment B type compound wherein Z=Cl, Br, OTos, OMs can be reacted with a fragment C type compound trough a base mediated coupling reaction. (Method 2) Possible bases to effect this reaction (but not limited to) are K$_2$CO$_3$, Cs$_2$CO$_3$, triethylamine, sodium hydride. A suitable solvent (but not limited to) for this type of base mediated coupling is DMF (dimethylformamide).

Fragment A type compounds can be generally prepared as depicted in scheme 2.

Scheme 2. General synthesis of fragment A type compounds

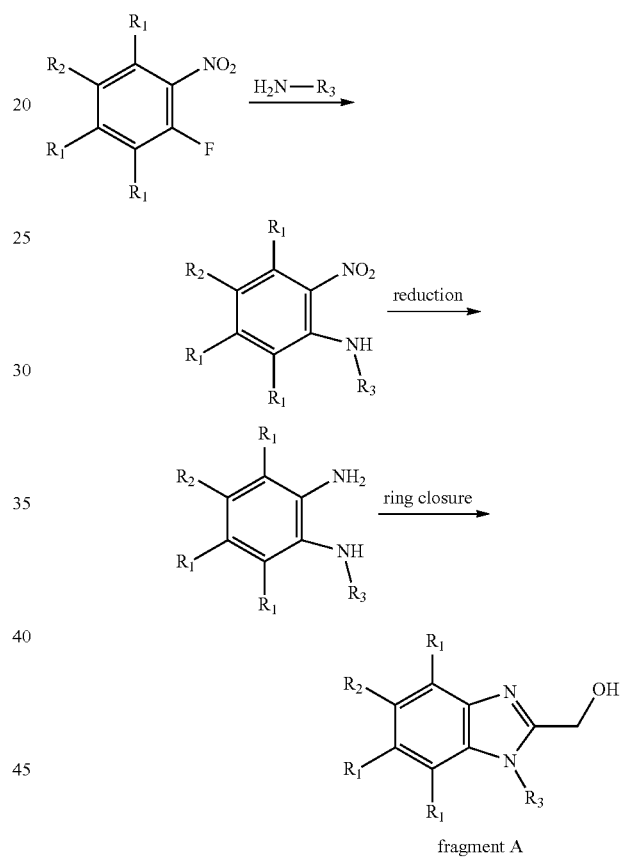

In general, fragment B type compounds can be prepared from fragment A type compounds trough reaction with reagents like (but not limited to) SOCl$_2$, PBr$_3$, p-TsCl, MsCl.

Scheme 3. General synthesis of fragment B type compounds

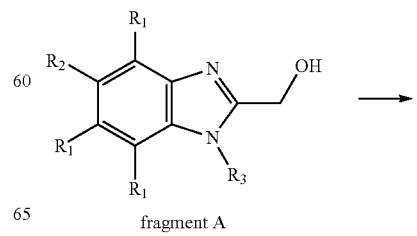

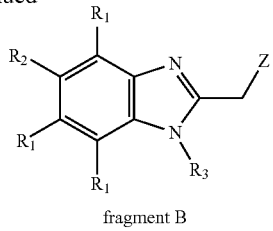

fragment B

Fragment C type compounds can be prepared as depicted in Scheme 4.

separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

Scheme 4. General synthesis of fragment B type compounds

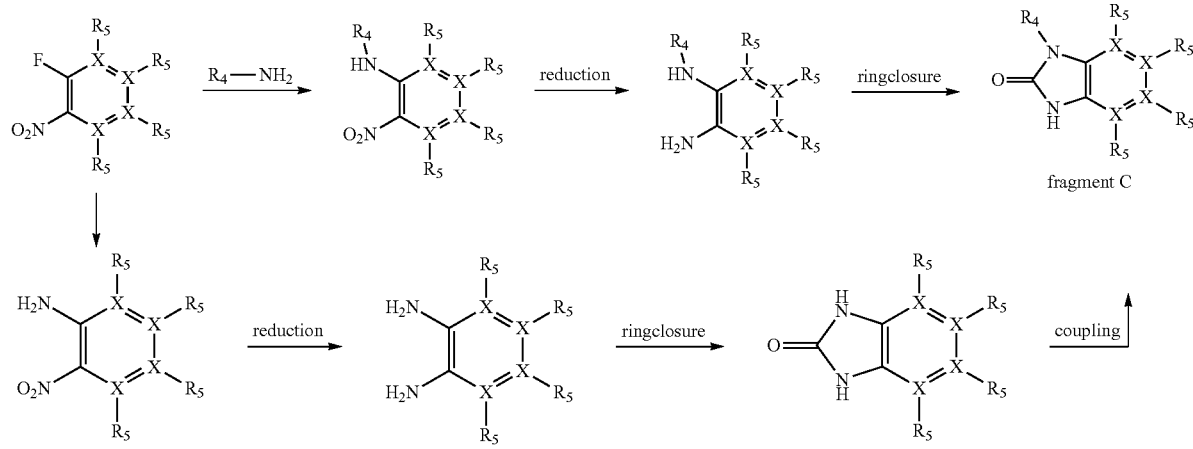

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I) which are sufficiently basic or acidic may be converted into the corresponding diastereomeric salt forms by reaction with a suitable chiral acid, respectively chiral base. Said diastereomeric salt forms are subsequently In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylaxictically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any embodiment thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any embodiment thereof, their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any embodiment thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any embodiment thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of formula (I), as specified herein, or of a compound of any of the subgroups of compounds of formula (I), as specified herein.

In general it is contemplated that an antivirally effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

The invention will hereinafter be illustrated with reference to the following, non-limiting examples.

Example 1

A detailed description of the synthesis of 3-({5-Bromo-1-[3-(methylsulfonyl)propyl]-1H-benzimidazol-2-yl}methyl)-1-cyclopropyl-1,3-dihydro-2H-imidazo[4,5-c]pyridin-2-one (P2), a representative example of the invention is given in Scheme 5.

Scheme 5

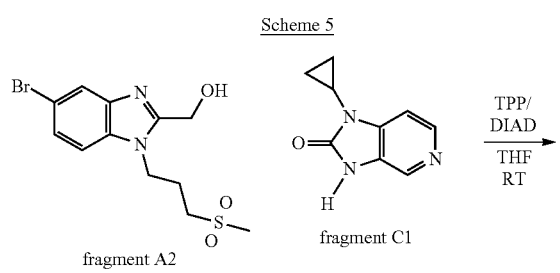

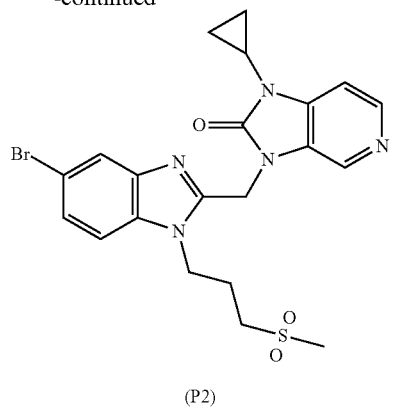

(P2)

In a 100 mL dry flask, fragment A2 (750 mg, 2.14 mmol), triphenylphosphine (645 mg, 2.46 mmol, 1.15 eq) and fragment C1 (393 mg, 2.25 mmol, 1.05 eq) were dissolved in tetrahydrofuran (THF) (60 mL). The solution was placed under N$_2$ atmosphere and diisopropylazodicarboxylate (DIAD) (0.484 mL, 2.46 mmol, 1.15 eq) was added via syringe. The reaction mixture was stirred at room temperature under nitrogen overnight. The mixture was evaporated to dryness and purified by preparative HPLC on an RP Vydac Denali C18 column (10 μm, 250 g, 5 cm) using a 0.25% NH$_4$HCO$_3$ in water-CH$_3$CN solution as the eluent. After evaporation and drying in vacuo, 620 mg (1.23 mmol, 57.5%) of a white solid was obtained.

The synthesis of {5-Bromo-1-[3-(methylsulfonyl)propyl]-1H-benzimidazol-2-yl}-methanol (fragment A2) was done as shown in scheme 6.

Scheme 6

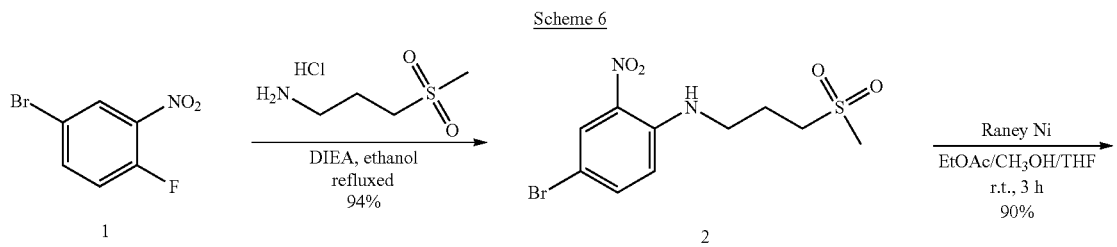

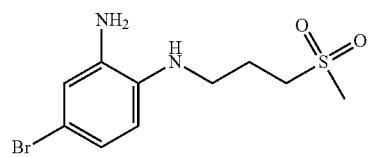

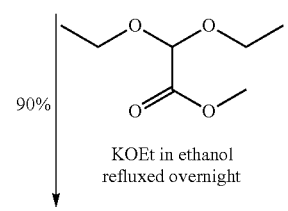

-continued

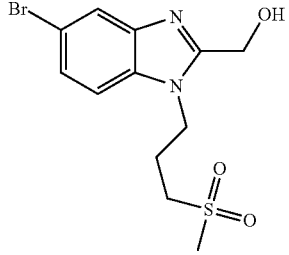

fragment A2

1) HCl, H₂O, THF, refluxed overnight.
2) NaBH₄, methanol, -10° C.
60%

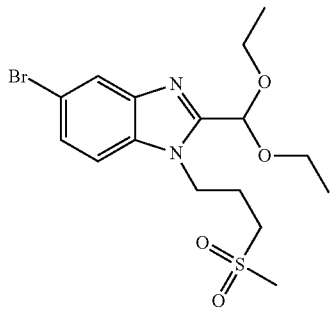

4

Compound 1 (7.6 g, 35 mmol), 3-(methylsulfonyl)propan-1-amine hydrochloride (6 g, 35 mmol) and diisopropylethylamine (DIEA) (13.5 g, 105 mmol) were dissolved in ethanol (70 mL) and refluxed for 14 h. The mixture was cooled to 20° C. The precipitate was filtered and washed with ethanol. 11 g (94%) of compound 2 was obtained as an orange powder. Compound 2 (10 g, 29.7 mmol) in methanol (200 mL), EtOAc (200 mL) and THF (200 mL) was hydrogenated with Raney Ni (10 g) as a catalyst at 20° C. (1 atm) for 3 h. After uptake of H₂ (3 eq), the catalyst was filtered off and the filtrate was evaporated. 10 g (90%) of compound 3 was obtained as a black solid. Compound 3 (10 g, 29.7 mmol) and methyl dimethoxyacetate (9.2 g, 68.31 mmol) in 24 wt % KOEt in ethanol (13.5 g, 38.5 mmol) were stirred and refluxed overnight. The mixture was evaporated under vacuum. Water (200 mL) was added. Acetic acid was added to neutralize the mixture. The mixture was extracted with ethyl acetate (2×100 mL). The combined organic layers were washed with saturated NaHCO₃, brine and dried over Na₂SO₄. The solvent was removed under vacuum to yield 12.3 g (90%) of compound 4 as dark oil. Compound 4 (12.3 g, 29.3 mmol) in THF (100 mL) was stirred for 0.5 h at 20° C. to dissolve. Conc. HCl (21 mL) and H₂O (42 mL) were added. The mixture was refluxed for 6 h and then cooled to -10° C. CH₃OH (50 mL) were added, followed by careful addition of NaBH₄ (24 g, 629 mmol). The mixture was stirred for 0.5 h at 10° C. and concentrated under vacuum. Water (200 mL) was added. The mixture was extracted with ethyl acetate (2×100 mL). The combined organic layers were washed with brine and dried over Na₂SO₄. The solvent was removed under vacuum. The resulting solid was washed with ethyl acetate (2×5 mL) and dried under vacuum. 6.8 g (60%) of fragment A2 was obtained as an off-white solid. m/z=347 & 349 (M+H)+Br pattern. ¹H NMR (400 MHz, DMSO-d₆) δ ppm 2.20 (dq, J=7.8, 7.5 Hz, 2H), 2.98 (s, 3H), 3.16-3.24 (m, 2H), 4.42 (t, J=7.4 Hz, 2H), 4.73 (d, J=6.0 Hz, 2H), 5.73 (t, J=5.8 Hz, 1H), 7.42 (dd, J=8.7, 1.9 Hz, 1H), 7.63 (d, J=8.5 Hz, 1H), 7.79-7.83 (m, 1H)

The synthesis of 1-(cyclopropyl)-1,3-dihydro-2H-imidazo[4,5-c]pyridin-2-one (fragment C1) was done as shown in scheme 7.

Scheme 7

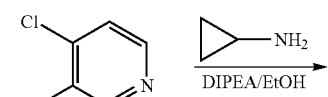

5

-continued

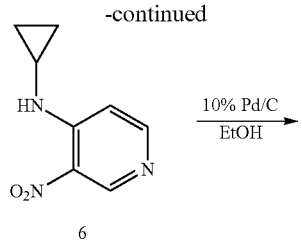

6

10% Pd/C
EtOH

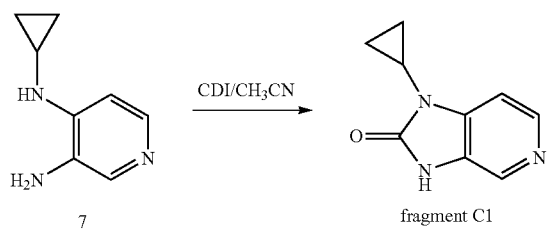

7      CDI/CH₃CN      fragment C1

A round-bottom flask was charged with 3-nitro-4-chloropyridine (600 g, 3.8 mol), absolute EtOH (3 L), diisopropylethylamine (DIPEA) (1320 mL, 7.6 mol) and cyclopropyl amine (432 g, 7.6 mol). The resulting solution was refluxed for 10 h. The reaction was cooled to 0° C., and the solid was collected by filtration. The filter cake was washed with cold ethanol (2×500 mL) to give compound 6. The mother liquor was concentrated and partitioned between water (1000 mL) and ethyl acetate (1000 mL). The aqueous layer was extracted with ethyl acetate (2×500 mL), dried over MgSO₄, filtered, and concentrated to give a second batch of product (total: 650 g, 96%). A suspension of compound 6 (650 g, 3.65 mol) and 10% Pd/C (50% water; 163 g) in EtOH (7 L) was hydrogenated at 50 psi H₂ for 16 h at room temperature. The suspension was filtered through Celite and concentrated. The residue was dried in vacuo to provide compound 7 (490 g, 90.6%). To a solution of compound 7 (490 g, 3.29 mol) in CH₃CN (4 L) at 0° C. was added carbonyldiimidazole (CDI) (559 g, 3.45 mol, 1.05 eq.), and the resulting mixture was warmed to room temperature and stirred for 16 h at room temperature. The precipitate was collected by filtration and the solid was washed with cold CH₃CN (2×1000 mL). The solid was dried in vacuo to give fragment C1. (450 g, 78.2%). m/z=176 (M+H). ¹H NMR (400 MHz, DMSO-d₆) δ ppm 0.84-0.91 (m, 2H), 0.98-1.06 (m, 2H), 2.89 (tt, J=7.0, 3.5 Hz, 1H), 7.18 (d, J=5.5 Hz, 1H), 8.16 (s, 1H), 8.19 (d, J=5.5 Hz, 1H), 10.98 (br. s., 1H).

Examples 2-27

Derivatives P1 and P3-P27 were prepared according to the methods described above for the synthesis of P2. Compounds P1-P27 were tested for RSV inhibitory activity (Table 1).

Example 28

Synthesis of 3-((5-chloro-1-(4-fluorobutyl)-1H-benzo[d]imidazol-2-yl)methyl)-1-(methylsulfonyl)-1H-imidazo[4,5-c]pyridin-2(3H)-one (P34)

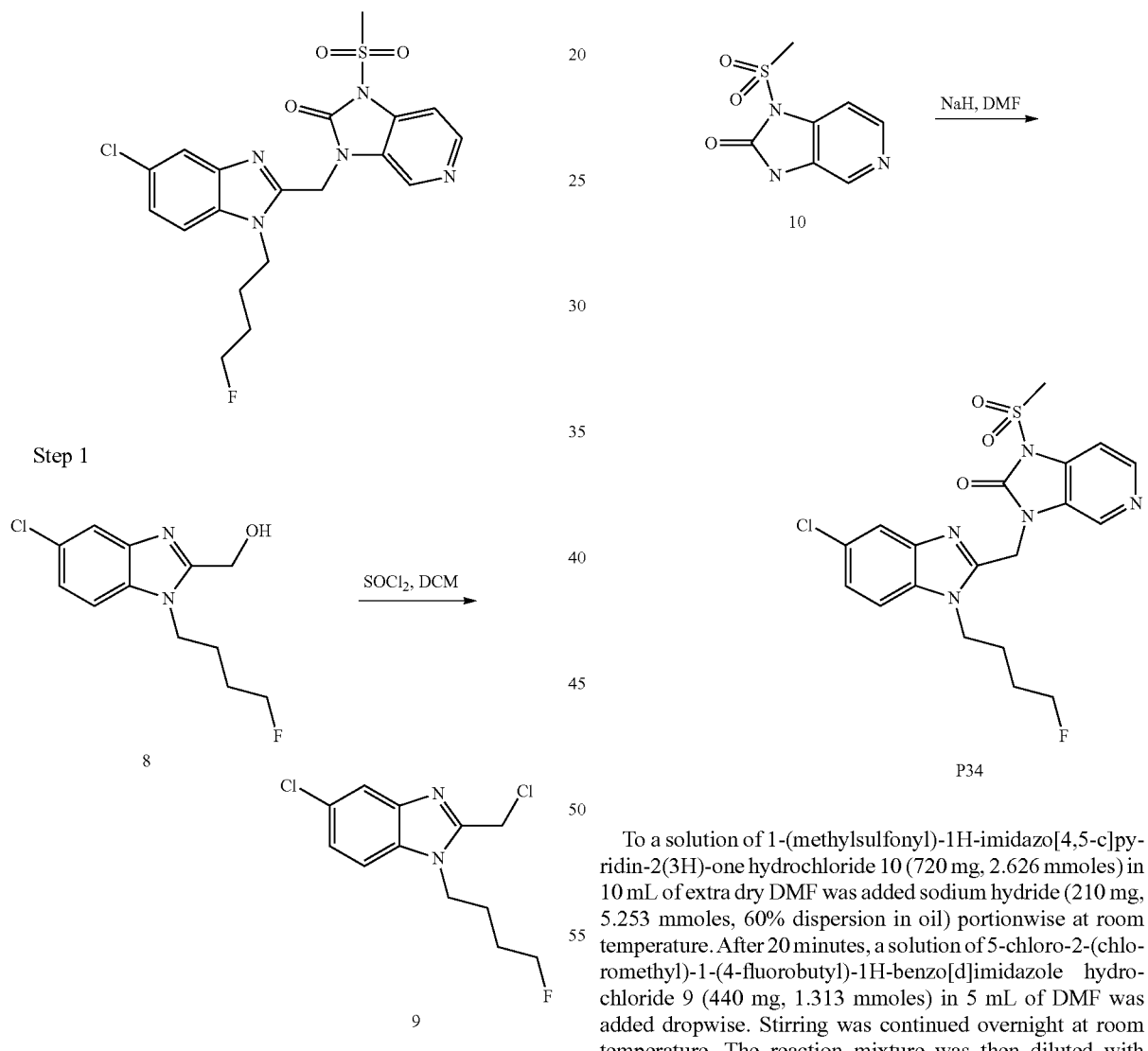

To a solution of alcohol 8 (363 mg, 1.414 mmole) in 30 mL of dichloromethane was added dropwise a solution of thionyl chloride (336 mg, 2 eq) in 10 mL of dichloromethane. The reaction mixture was stirred for one hour at 45° C. It was then concentrated under vacuum to give the desired intermediate 9 (440 mg, 99%) as an HCl salt, which was used as such in the next step.

To a solution of 1-(methylsulfonyl)-1H-imidazo[4,5-c]pyridin-2(3H)-one hydrochloride 10 (720 mg, 2.626 mmoles) in 10 mL of extra dry DMF was added sodium hydride (210 mg, 5.253 mmoles, 60% dispersion in oil) portionwise at room temperature. After 20 minutes, a solution of 5-chloro-2-(chloromethyl)-1-(4-fluorobutyl)-1H-benzo[d]imidazole hydrochloride 9 (440 mg, 1.313 mmoles) in 5 mL of DMF was added dropwise. Stirring was continued overnight at room temperature. The reaction mixture was then diluted with water (50 mL) and extracted with EtOAc (2×50 mL). The organic layers were combined, washed with brine, dried over MgSO4, filtered and concentrated under vacuum. The resulting slightly orange oil was triturated in DCM and the precipitate was filtered off. It was further washed with DCM, then isopropylether and dried under high vacuum, to provide the title product 3-((5-chloro-1-(4-fluorobutyl)-1H-benzo[d]

imidazol-2-yl)methyl)-1-(methylsulfonyl)-1H-imidazo[4,5-c]pyridin-2(3H)-one P34 as a white solid in 40% yield; m/z=452 (M+H)+.

Example 29

Synthesis of 4-(5-chloro-2-((1-cyclopropyl-2-oxo-1H-imidazo[4,5-c]pyridin-3(2H)-yl)methyl)-1H-benzo[d]imidazol-1-yl)butanoic acid (P45)

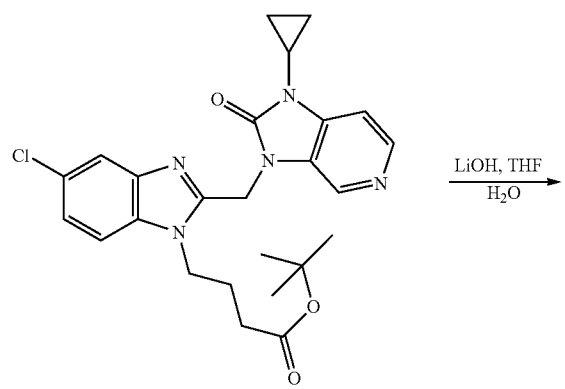

P52

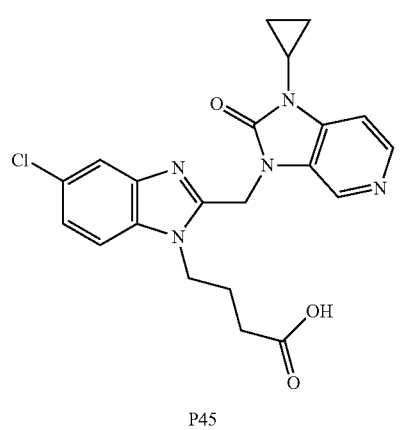

P45

To compound P52 (2.8 g, 5.8 mmol) dissolved in THF (100 mL), was added lithium hydroxide (556 mg, 23 mmol) dissolved in water (25 mL). The resulting mixture was stirred at room temperature overnight. The reaction mixture was then poured into water, acidified to pH 4 with a 1M aqueous solution of hydrochloric acid. The resulting mixture was extracted with dichloromethane. The organic layer was dried over MgSO4 and concentrated. The residue was purified by column chromatography using dichloromethane and methanol to give the title compound P45 as a white powder (2.37 g, 84%); m/z=426 (M+H)+.

Example 30

Synthesis of 3-((5-bromo-1-(4-morpholino-4-oxobutyl)-1H-benzo[d]imidazol-2-yl)-methyl)-1-cyclopropyl-1H-imidazo[4,5-c]pyridin-2(3H)-one (P48)

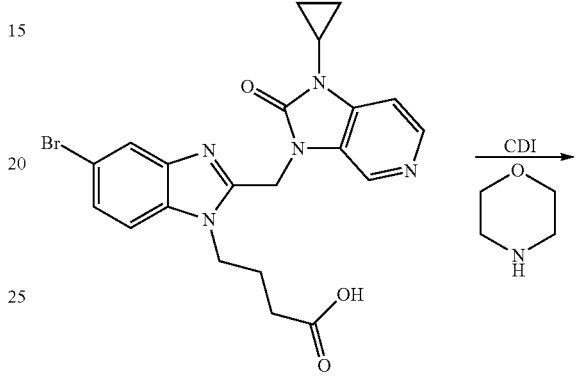

P84

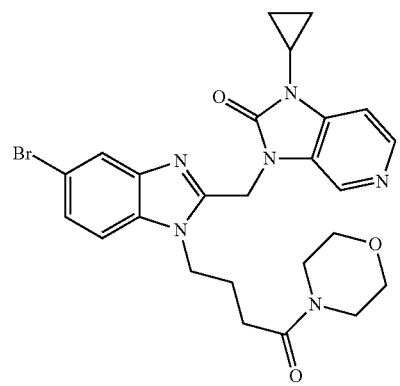

P48

To the carboxylic acid P84 (500 mg, 1 mmol) dissolved in acetonitrile ((50 mL) was added carbonyl diimidazole (207 mg, 2.3 mmol) in one portion. The mixture was stirred at 50° C. overnight. It was then allowed to cool down to room temperature and morpholine (278 mg, 3.2 mmol) was added. The resulting mixture was stirred at room temperature for 4 hours, then poured into water (50 mL) and extracted with dichloromethane (30 mL). The organic layer was dried over MgSO4 then concentrated. The residue was purified by column chromatography using dichloromethane and methanol. The product P48 was isolated as a white powder (200 mg, 34%); m/z=540 (M+H)+.

Example 31

Synthesis of 4-(5-chloro-2-((1-cyclopropyl-2-oxo-1H-imidazo[4,5-c]pyridin-3 (2H)-yl)methyl)-1H-benzo[d]imidazol-1-yl)-N-(cyclopropylsulfonyl)butanamide (P49)

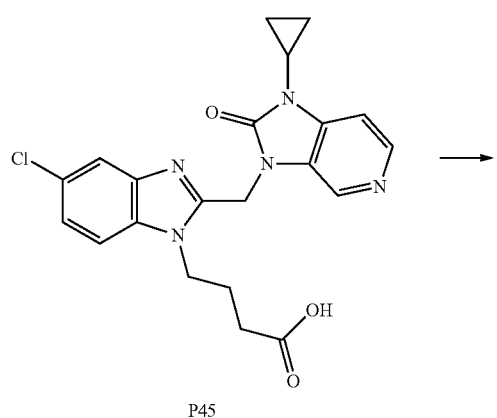

To a solution of P45 (500 mg, 1.17 mmol) in acetonitrile (50 mL) was added carbonyl diimidazole (210 mg, 1.3 mmol). The resulting mixture was stirred at 50° C. for 2 hours. It was then allowed to cool down to room temperature and cyclopropane sulfonamide (157 mg, 1.29 mmol) and DBU (268 mg, 1.76 mmol) were added successively. The reaction mixture was stirred at room temperature overnight. The resulting mixture was poured in water (50 mL) then dichloromethane (50 mL) was added. The mixture was acidified with a 1M solution of hydrochloric acid until pH 4 then extracted with dichloromethane. The organic layer was dried over MgSO4 then concentrated. The residue was purified by column chromatography to yield P49 (487 mg, 78%) as a white powder; m/z=544 (M+H)+.

Example 32

Synthesis of 3-({5-chloro-1-[3-(1H-imidazol-1-yl)propyl]-1H-benzimidazol-2-yl}methyl)-1-cyclopropyl-1,3-dihydro-2H-imidazo[4,5-c]pyridin-2-one (P51)

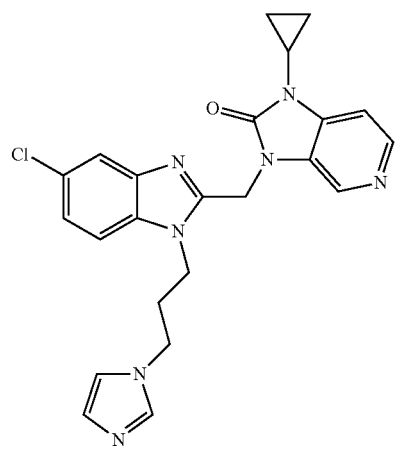 [SMILES: O=c1n(Cc2nc3cc(Cl)ccc3n2CCCn2ccnc2)c2cnccc2n1C1CC1]

Step 1

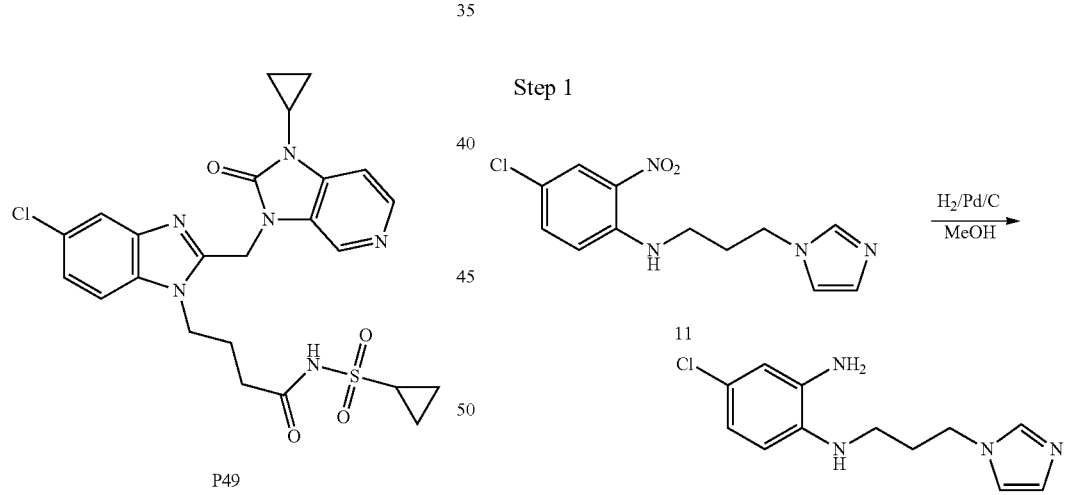

4-chloro-N-[3-(1H-imidazol-1-yl)propyl]-2-nitroaniline (11, 5 g, 17.8 mmol) was dissolved in 100 mL methanol (MeOH) and Palladium on activated carbon (10%, 120 mg, 0.1 eq.) was added under nitrogen atmosphere. The solution was hydrogenated at 1 bar for 16 hours. The reaction was filtered over celite and the filtrate concentrated in vacuo and purified by flash chromatography (gradient 0 to 10% methanol in CH2Cl2) to give 4-chloro-N1-[3-(1H-imidazol-1-yl)propyl]benzene-1,2-diamine (12, 2.18 g, 49%) as a solid; LCMS m/z=251 (M+H)+

Step 2

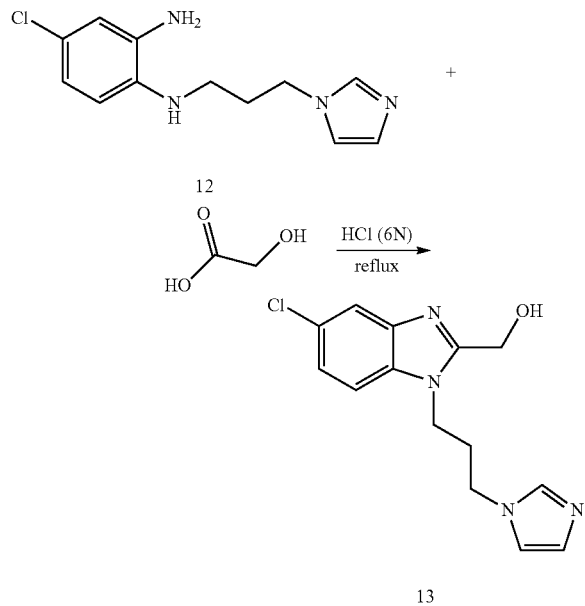

Glycolic acid (1.98 g, 26 mmol, 3 eq.) was added to a solution of 4-chloro-N[1]-[3-(1H-imidazol-1-yl)propyl]benzene-1,2-diamine (12, 2.18 g, 8.7 mmol) in HCl (6N, 20 mL) at room temperature. The reaction mixture was heated up until 90° C. during 16 hours. After cooling to ambient temperature the reaction mixture was diluted with 100 mL water followed by addition of NaHCO$_3$ until the pH was approximately 7. CH$_2$Cl$_2$ (30 ml) was added and the organic layer was separated and the aqueous layer was further extracted with additional CH$_2$Cl$_2$ (20 mL). The combined organic layers were dried (MgSO$_4$), filtered and concentrated in vacuo and purified by flash chromatography (0 to 10% MeOH in CH$_2$Cl$_2$) to give {5-chloro-1-[3-(1H-imidazol-1-yl)propyl]-1H-benzimidazol-2-yl}methanol (13, 740 mg, 30%) as a white solid; LCMS m/z=291 (M+H)$^+$ Step 3

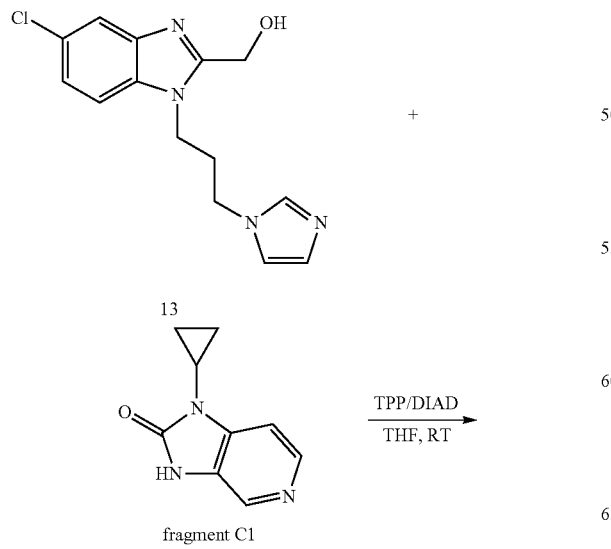

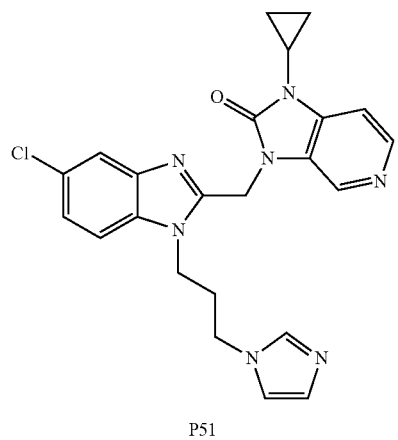

In a 100 mL flask, {5-chloro-1-[3-(1H-imidazol-1-yl)propyl]-1H-benzimidazol-2-yl}methanol (13) (740 mg, 2.54 mmol), triphenylphosphine (667.5 mg, 2.54 mmol, 1 eq.) and 1-cyclopropyl-1,3-dihydro-2H-imidazo[4,5-c]pyridin-2-one (fragment C1) (443.3 mg, 2.54 mmol, 1 eq.) were dissolved in tetrahydrofuran (THF) (60 mL). The solution was placed under N2 atmosphere and diisopropylazodicarboxylate (DIAD) (0.752 mL, 3.8 mmol, 1.5 eq.) was added via syringe. The reaction mixture was stirred at room temperature under nitrogen during 16 hours. The mixture was evaporated to dryness and purified by preparative HPLC on an RP SunFire Prep C18 column (OBD-10 µm, 30×150 mm) using a 0.25% NH4HCO3 in water-CH3CN solution as eluent. After evaporation and drying in vacuo, 3-({5-chloro-1-[3-(1H-imidazol-1-yl)propyl]-1H-benzimidazol-2-yl}methyl)-1-cyclopropyl-1,3-dihydro-2H-imidazo[4,5-c]pyridin-2-one (P51, 635 mg, 58%) was obtained as a white solid; LCMS m/z=448 (M+H)+

Example 33

Synthesis of 4-(5-chloro-2-((1-cyclopropyl-2-oxo-1H-imidazo[4,5-c]pyridin-3(2H)-yl)methyl)-1H-benzo[d]imidazol-1-yl)-N-(cyclopropylsulfonyl)-N-methylbutanamide (P59)

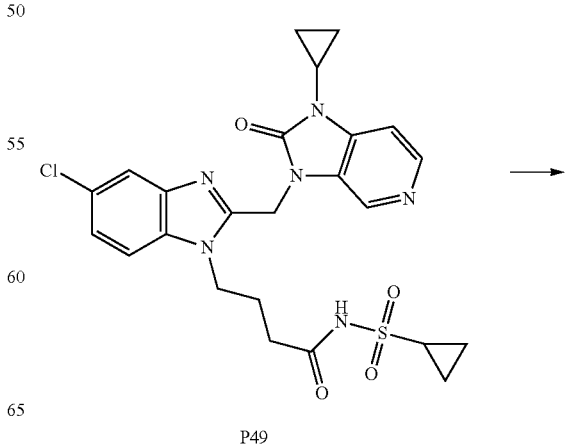

-continued

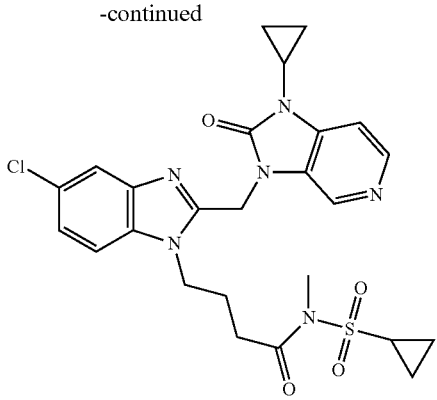

P59

To a solution of P49 (500 mg, 0.94 mmol) in DMF (50 mL) was added cesium carbonate (616 mg, 1.9 mmol). The resulting mixture was stirred at room temperature for 1 hour then methyl iodide (0.059 mL, 1.9 mmol) was added. The resulting mixture was stirred at room temperature overnight. The mixture was poured in water then extracted with dichloromethane, dried over MgSO$_4$ and concentrated. The residue was purified by column chromatography using dichloromethane and methanol to yield P59 (120 mg, 21%) as a white powder; m/z=544 (M+H)$^+$.

Example 34

Synthesis of (3-{[5-chloro-1-(4-fluorobutyl)-1H-benzimidazol-2-yl]methyl}-2-oxo-2,3-dihydro-1H-imidazo[4,5-c]pyridin-1-yl)acetic acid (P67)

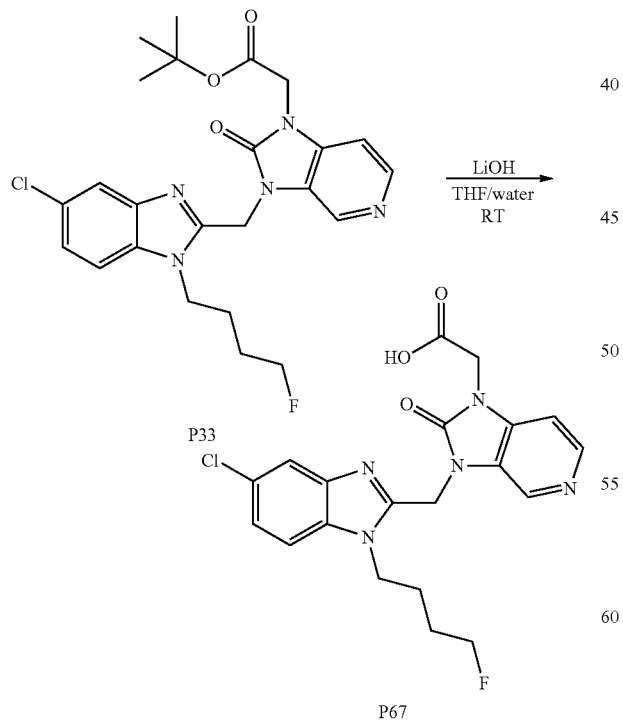

In a 100 mL dry flask, tert-butyl (3-{[5-chloro-1-(4-fluorobutyl)-1H-benzimidazol-2-yl]methyl}-2-oxo-2,3-dihydro-1H-imidazo[4,5-c]pyridin-1-yl)acetate (P33) (1.74 g, 3.49 mmol) was dissolved in 50 mL tetrahydrofuran/water mixture (3/1). Lithium hydroxide (167.3 mg, 6.98 mmol, 2 eq.) was added to the solution and the mixture was stirred for 16 hours at room temperature. The reaction mixture was diluted with water (20 mL) followed by the addition of aqueous HCl (1M) until the pH was approximately 6. Dichloromethane (40 mL) was added to the reaction mixture and the organic layer separated. The aqueous layer was evaporated to dryness and dried into the oven during 16 hours to give (3-{[5-chloro-1-(4-fluorobutyl)-1H-benzimidazol-2-yl]methyl}-2-oxo-2,3-dihydro-1H-imidazo[4,5-c]pyridin-1-yl) acetic acid (P67, 1.6 g, 100%) as a white solid; LCMS m/z=432 (M+H)$^+$ Example 35

Synthesis of 2-(3-{[5-chloro-1-(4-fluorobutyl)-1H-benzimidazol-2-yl]methyl}-2-oxo-2,3-dihydro-1H-imidazo[4,5-c]pyridin-1-yl)-N-cyclopropylacetamide (P68

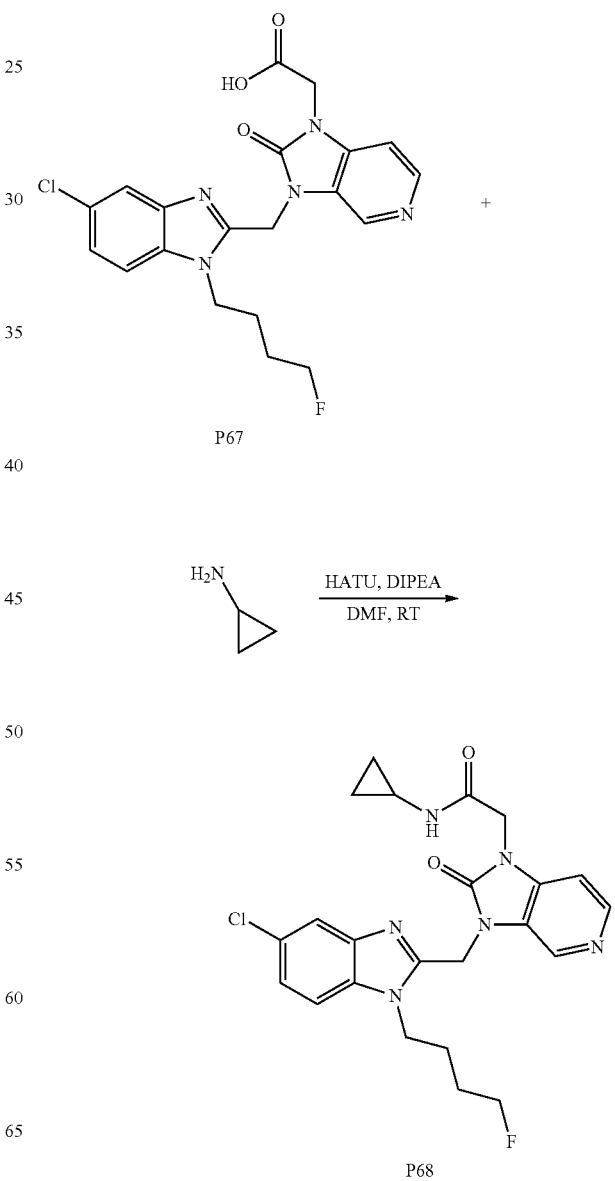

In a 100 ml dry flask, (3-{[5-chloro-1-(4-fluorobutyl)-1H-benzimidazol-2-yl]methyl}-2-oxo-2,3-dihydro-1H-imidazo[4,5-c]pyridin-1-yl)acetic acid (P67, 300 mg, 0.69 mmol), diisopropylethylamine (0.29 mL, 2.08 mmol, 3 eq.), cyclopropylamine (60 μL, 0.83 mmol, 1.2 eq.) and 2-(1H-7-Azabenzotriazol-1-yl)-1,1,3,3-tetramethyl uronium hexafluorophosphate Methanaminium (HATU, 316.9 mg, 0.83 mmol, 1.2 eq.) were dissolved in DMF (50 mL). The solution was placed under N$_2$ atmosphere and stirred at room temperature during 1 hour. The reaction mixture was diluted with water (20 ml) and extracted with dichloromethane (50 mL). The organic layer was dried with MgSO$_4$ and evaporated. The residue was further crystallized in diisopropylether/acetonirile. The solid was filtered off and dried into the oven for 16 hours which gave 2-(3-{[5-chloro-1-(4-fluorobutyl)-1H-benzimidazol-2-yl]methyl}-2-oxo-2,3-dihydro-1H-imidazo[4,5-c]pyridin-1-yl)-N-cyclopropylacetamide (P68, 86 mg, 26%) as a white solid; LCMS m/z=471 (M+H)$^+$ Example 36

Synthesis of 4-(5-bromo-2-((1-cyclopropyl-2-oxo-1H-imidazo[4,5-c]pyridin-3(2H)-yl)methyl)-1H-benzo[d]imidazol-1-yl)-N-sulfamoylbutanamide (P76)

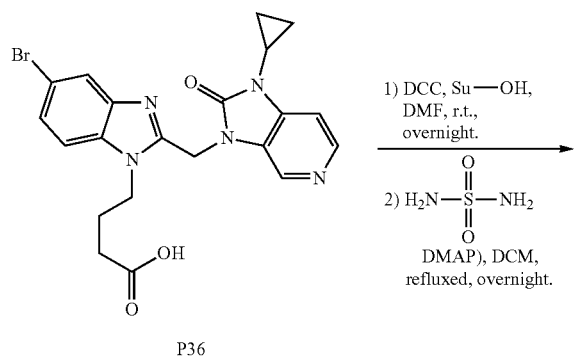

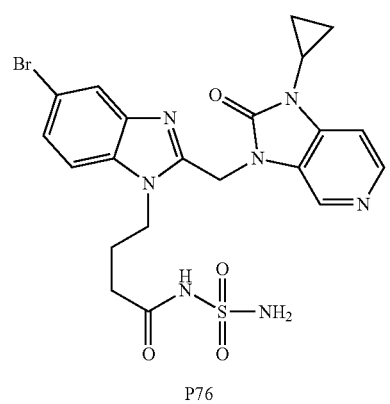

Compound P36 (4.5 g, 9.57 mmol), DCC (2.0 g, 9.57 mmol) and SuOH (1.4 g, 12.4 mmol) in DMF (50 ml) were stirred for 14 h at 20° C. The mixture was then poured into ice-water (100 ml). The mixture was extracted with CH2Cl2 (2*100 ml). The organic layers were washed with brine, dried over MgSO4, filtered and evaporated under vacuum to give 4.5 g of intermediate which was used in the next step without further purification.

The previous intermediate (1.0 g, 1.76 mmol), sulfonamide (0.51 g, 5.3 mmol) and DMAP (0.65 g, 5.3 mmol) in CH$_2$Cl$_2$ (10 ml) were stirred and refluxed for 14 h. The mixture was then evaporated under vacuum. The residue was purified by high-performance liquid chromatography (C18, eluent: CH3CN/H2O from 15/85 to 35/65 with 10 mmol/L HCl as buffer). The pure fractions were collected and the organic solvent was evaporated. 10% NaHCO3 was added until pH=8. The mixture was filtered off and the solid was washed with H2O (2*10 mL). The product was obtained by lyophilization (80 mg, yield 10%).

1H NMR (400 MHz, DMSO-d) d ppm 0.88-0.94 (m, 2H) 1.03-1.10 (m, 2H) 1.82-1.92 (m, 2H) 2.20-2.28 (m, 2H) 2.97 (q, J=3.47 Hz, 1H) 4.34 (t, J=7.98 Hz, 2H) 5.42 (s, 2H) 7.29 (d, J=5.10 Hz, 1H) 7.40 (dd, J1=8.68 Hz, J2=1.74 Hz, 1H) 7.63 (d, J=8.68, 1H) 7.80 (d, J=1.74 Hz, 1H) 8.26 (d, J=5.20 Hz, 1H) 8.38 (s, 1H)

Examples 37-85

Derivatives P28-33, P35-44, P46, 47, 50, P52-58, P60-66, P69-75 and P77-P85 were prepared according to the methods described above.

All compounds P28-83 were tested for RSV inhibitory activity (Table 2).

Examples 86-89

Derivatives P86-P89 are prepared according to the methods described above and/or according to methods known in the art (Table 3).

General Experimental Details

HPLC-MS analysis was done using either one of the following methods:

Method 1:

The HPLC measurement was performed using an Agilent 1100 module comprising a pump, a diode-array detector (DAD) (wavelength used 220 nm), a column heater and a column as specified below. Flow from the column was split to an Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min. Reversed phase HPLC was carried out on a YMC-Pack ODS-AQ, 50×2.0 mm 5 mm column with a flow rate of 0.8 mL/min. Two mobile phases (mobile phase A: water with 0.1% TFA; mobile phase B: acetonitrile with 0.05% TFA) were used. First, 100% A was hold for 1 minute. Then a gradient was applied to 40% A and 60% B in 4 minutes and hold for 2.5 minutes. Typical injection volumes of 2 mL were used. Oven temperature was 50° C. (MS polarity: positive)

Method 2:

The HPLC measurement was performed using an Agilent 1100 module comprising a pump, a diode-array detector (DAD) (wavelength used 220 nm), a column heater and a column as specified below. Flow from the column was split to a Agilent MSD Series G1946C and G1956A. MS detector was configured with API-ES (atmospheric pressure electrospray ionization). Mass spectra were acquired by scanning from 100 to 1000. The capillary needle voltage was 2500 V for positive ionization mode and 3000 V for negative ionization mode. Fragmentation voltage was 50 V. Drying gas temperature was maintained at 350° C. at a flow of 10 l/min. Reversed phase HPLC was carried out on a YMC-Pack ODS-AQ, 50×2.0 mm 5 mm column with a flow rate of 0.8 mL/min. Two mobile phases (mobile phase A: water with 0.1% TFA; mobile phase B: acetonitrile with 0.05% TFA) were used. First, 90% A and 10% B was hold for 0.8 minutes. Then a gradient was applied to 20% A and 80% B in 3.7 minutes and hold for 3 minutes. Typical injection volumes of 2 mL were used. Oven temperature was 50° C. (MS polarity: positive)

Method 3:

Column. XTerra MS C18 2.5μ, 4.6×50 mm, mobile phase A: 10 mM NH$_4$OOCH+0.1% HCOOH in H$_2$O, mobile phase B: MeOH operating at a column temperature of 50° C. using a flow rate of 1.5 mL/min. Gradient conditions: t=0 min: 65% A, 35% B; t=3.5 min, 5% A, 95% B; t=5.5 min, 5% A, 95% B; t=5.6 min: 65% A, 35% B; t=7 min, 65% A, 35% B.

Method 4:

Column: SunFire C18 3.5μ6×100 mm, mobile phase A: 10 mM NH$_4$OOCH+0.1% HCOOH in H$_2$O, mobile phase B: MeOH operating at a column temperature of 50° C. using a flow rate of 1.5 mL/min. Gradient conditions: t=0 min: 65% A, 35% B; t=7 min, 5% A, 95% B; t=9.6 min, 5% A, 95% B; t=9.8 min: 65% A, 35% B; t=12 min, 65% A, 35% B.

NMR spectra were recorded on a Bruker 400 spectrometer, operating at 400 MHz for $^1$H. Chemical shifts are given in ppm and a J value in Hz. Multiplicity is indicated using the following abbreviations: d for doublet, t for a triplet, m for a multiplet, etc. Thin-layer chromatography (TLC) was performed on 5×10 cm aluminium sheets coated with Silicagel 60 F$_{254}$ (Merck KGaA).

Antiviral Activity

Black 96-well clear-bottom microtiter plates (Corning, Amsterdam, The Netherlands) were filled in duplicate using a customized robot system with serial 4-fold dilutions of compound in a final volume of 50 μl culture medium [RPMI medium without phenol red, 10% FBS, 0.04% gentamycin (50 mg/mL) and 0.5% DMSO]. Then, 100 μl of a HeLa cell suspension (5×10$^4$ cells/mL) in culture medium was added to each well followed by the addition of 50 μl rgRSV224 (MOI=0.02) virus in culture medium using a multidrop dispenser (Thermo Scientific, Erembodegem, Belgium). rgRSV224 virus is an engineered virus that includes an additional GFP gene (Hallak et al, 2000) and was in-licensed from the NIH (Bethesda, Md., USA). Medium, virus- and mock-infected controls were included in each test. Cells were incubated at 37° C. in a 5% CO$_2$ atmosphere. Three days post-virus exposure, viral replication was quantified by measuring GFP expression in the cells by a MSM laser microscope (Tibotec, Beerse, Belgium). The EC$_{50}$ was defined as the 50% inhibitory concentration for GFP expression. In parallel, compounds were incubated for three days in a set of white 96-well microtiter plates (Corning) and the cytotoxicity of compounds in HeLa cells was determined by measuring the ATP content of the cells using the ATPlite kit (PerkinElmer, Zaventem, Belgium) according to the manufacturer's instructions. The CC$_{50}$ was defined as the 50% concentration for cytotoxicity.

REFERENCES

Hallak L K, Spillmann D, Collins P L, Peeples M E. Glycosaminoglycan sulfation requirements for respiratory syncytial virus infection. J. Virol. 740, 10508-10513 (2000).

Assessment of Cardiovascular Safety

The effects on cardio-hemodynamic and cardio-electrophysiological parameters of compounds described here and the reference compound BMS-433771 were assessed in anesthetized guinea-pigs. For that purpose, the characteristics of the surface electrocardiogram (ECG), heart rate and mean arterial blood pressure were measured in two groups of experiments. In the first group (n=7), increasing doses of assessed compound (0.32, 0.64, 1.25, 2.5, 5 and 10 mg/kg) were administered i.v. over a period of 5 min at 15-min intervals. In the second group (n=7), corresponding volumes of vehicle were administered according to the same protocol. This experimental model is known to readily detect ECG effects induced by compounds which produce cardiac electrophysiological changes, including prolongation of the QTc interval, similar to those expected in man (De Clerck, F, Fundam. Clin. Pharm.; 2002; 16: 125-139; Testai J. Appl. Toxicol.; 2004; 24: 217-222).

Concentrations leading to a significant QTcB prolongation (p<0.05) in the anesthetized guinea-pig model were 3.5 μM A with reference compound BMS-433771, while a representative compound according to the present invention only showed significant prolongation at concentrations above 18 μM (P6).

TABLE 1 formula (I)

[Structure of formula (I): a benzimidazolone-type compound with substituents R1, R2, R3, R4, R5 and X as shown]

| | R1 | R2 | R3 | R4 | X—R5 | 1H NMR | WT activity EC50 (nM) | Tox CC50 (μM) |
|---|---|---|---|---|---|---|---|---|
| P1 | H | Br | (CH2)4-F chain | cyclopropyl | N | 1H NMR (400 MHz, CHLOROFORM-d) δ ppm 0.97-1.06 (m, 2 H), 1.12-1.21 (m, 2 H), 1.61-1.82 (m, 4 H), 2.92 (tdd, J = 7.0, 7.0, 3.6, 3.5 Hz, 1 H), 4.34 (t, J = 7.0 Hz, 2 H), 4.43 (dt, J = 48.0, 5.0 Hz, 2 H), 5.35 (s, 2 H), 7.13 (dd, J = 5.3, 0.8 Hz, 1 H), 7.19 (d, J = 8.8 Hz, 1 H), 7.38 (dd, J = 8.7, 1.9 Hz, 1 H), 7.91 (d, J = 1.5 Hz, 1 H), 8.33 (d, J = 5.3 Hz, 1 H), 8.65 (s, 1 H) | 0.033 | >9.83603 |
| P2 | H | Br | (CH2)3-S(O)2CH3 | cyclopropyl | N | 1H NMR (400 MHz, DMSO-d6) δ ppm 0.87-0.98 (m, 2 H), 1.07 (m, J = 5.3 Hz, 2 H), 2.14 (ddd, J = 15.2, 7.8, 7.7 Hz, 2 H), 3.01 (s, 3 H), 3.23 (m, J = 15.3 Hz, 2 H), 4.49 (t, J = 7.4 Hz, 2 H), 5.35-5.49 (m, 2 H), 7.30 (d, J = 5.3 Hz, 1 H), 7.44 (dd, J = 8.5, 1.5 Hz, 1 H), 7.65 (d, J = 8.8 Hz, 1 H), 7.82 (d, J = 1.5 Hz, 1 H), 8.27 (d, J = 5.3 Hz, 1 H), 8.37-8.51 (m, 1 H) | 0.034 | >9.83603 |
| P3 | H | Br | (CH2)3-S(O)2CH3 | cyclopropyl | C—F | 1H NMR (400 MHz, CHLOROFORM-d) δ ppm 1.01 (br. s., 2 H), 1.09-1.17 (m, 2 H), 2.11-2.25 (m, 2 H), 2.85-2.96 (m, 1 H), 2.90 (s, 3 H), 3.01-3.13 (m, 2 H), 4.47-4.59 (m, 2 H), 5.28 (s, 2 H), 6.77-6.86 (m, 0 H), 7.06-7.13 (m, 0 H), 7.23-7.30 (m, 1 H), 7.27 (d, J = 4.8 Hz, 1 H), 7.41 (dd, J = 8.7, 1.9 Hz, 1 H), 7.94 (d, J = 1.5 Hz, 1 H) | 0.47 | >9.83603 |
| P4 | H | Br | (CH2)4-CN chain | cyclopropyl | N | 1H NMR (400 MHz, CHLOROFORM-d) δ ppm 0.97-1.05 (m, 2 H), 1.14-1.22 (m, 2 H), 1.67-1.78 (m, 3 H), 1.80-1.92 (m, 2 H), 2.39 (t, J = 6.8 Hz, 2 H), 2.96 (m, J = 6.9, 3.4, 3.3 Hz, 1 H), 2.95-2.98 (m, 1 H), 4.37 (t, J = 7.4 Hz, 2 H), 5.33 (s, 2 H), 7.14 (d, J = 5.0 Hz, 1 H), 7.19 (d, J = 8.8 Hz, 1 H), 7.39 (dd, J = 8.8, 1.8 Hz, 1 H), 7.92 (d, J = 5.0 Hz, 1H), 8.34 (d, J = 5.0 Hz, 1 H), 8.72 (s, 1 H) | 0.077 | >9.83603 |
| P5 | H | Br | (CH2)4-NH-S(O)2CH3 | cyclopropyl | N | 1H NMR (400 MHz, DMSO-d6) δ ppm 0.92 (s, 2 H), 1.07 (m, J = 5.5 Hz, 2 H), 1.44-1.57 (m, 2 H), 1.63-1.81 (m, 2 H), 2.88 (s, 3 H), 2.99 (s, 3 H), 4.35 (t, J = 7.5 Hz, 2 H), 5.40 (s, 2 H), 7.01 (t, J = 5.5 Hz, 1 H), 7.29 (d, J = 5.3 Hz, 1 H), 7.40 (dd, J = 8.5, 1.6 Hz, 1 H), 7.62 (d, J = 8.5 Hz, 1 H), 7.81 (d, J = 1.8 Hz, 1 H), 8.26 (d, J = 5.3 Hz, 1 H), 8.39 (s, 1 H) | <0.150 | >100.839 |

TABLE 1-continued formula (I)

| | $R_1$ | $R_2$ | $R_3$ | $R_4$ | $X-R_5$ | $^1$H NMR | WT activity $EC_{50}$ (nM) | Tox $CC_{50}$ (μM) |
|---|---|---|---|---|---|---|---|---|
| P6 | H | Cl |  |  | N | $^1$H NMR (400 MHz, CHLOROFORM-d) δ ppm 1.02 (m, J = 3.7, 1.8, 1.8 Hz, 2 H), 1.16 (m, J = 6.9, 1.9 Hz, 2 H), 2.22 (quin, J = 7.5 Hz, 2 H), 2.93 (s, 3 H), 2.95 (m, J = 7.0 Hz, 1 H), 3.10 (t, J = 7.4 Hz, 2 H), 4.42-4.62 (m, 2 H), 5.34 (s, 2 H), 7.15 (dd, J = 5.3, 0.8 Hz, 1 H), 7.27-7.34 (m, 2 H), 7.76 (dd, J = 1.8, 0.8 Hz, 1 H), 8.35 (d, J = 5.3 Hz, 1 H), 8.70 (s, 1 H) | <0.150 | >9.83603 |
| P7 | H | Br |  |  | C—H | $^1$H NMR (400 MHz, CHLOROFORM-d) δ ppm 0.99-1.06 (m, 2 H), 1.10-1.17 (m, 2 H), 2.16 (m, J = 7.6, 7.6, 7.6, 7.6 Hz, 2 H), 2.85 (s, 3 H), 2.93 (m, J = 6.9, 6.9, 3.5 Hz, 1 H), 3.04 (t, J = 7.5 Hz, 2 H), 4.49-4.56 (m, 2 H), 5.32 (s, 1 H), 5.32 (s, 2 H), 7.09 (m, J = 7.0, 7.0, 1.5 Hz, 1 H), 7.18-7.23 (m, 1 H), 7.24-7.29 (m, 1 H), 7.37-7.46 (m, 2 H), 7.93 (d, J = 1.8 Hz, 1 H) | <0.150 | >9.83603 |
| P8 | H | Br |  |  | N | $^1$H NMR (400 MHz, CHLOROFORM-d) δ ppm 0.97-1.06 (m, 2 H), 1.11-1.21 (m, 2 H), 1.71-1.86 (m, 6 H), 2.94 (m, J = 7.0, 3.4, 3.4 Hz, 1 H), 3.45-3.57 (m, 2 H), 4.29-4.39 (m, 2 H), 5.34 (s, 2 H), 7.13 (dd, J = 5.3, 0.8 Hz, 1 H), 7.20 (d, J = 8.5 Hz, 1 H), 7.27 (s, 1 H), 7.39 (dd, J = 8.7, 1.9 Hz, 1 H), 7.92 (d, J = 1.5 Hz, 1 H), 8.33 (d, J = 5.3 Hz, 1 H), 8.67 (d, J = 0.5 Hz, 1 H) | <0.205 | >9.83603 |
| P9 | H | Br |  |  | N | $^1$HNMR (400 MHz, CHLOROFORM-d) δ ppm 0.90-1.00 (m, 2 H), 1.11 (m, J = 6.0 Hz, 2 H). 1.91-2.05 (m, 2 H), 2.84-2.96 (m, 4 H), 3.12-3.24 (m, 2 H), 4.34 (t, J = 7.5 Hz, 2 H), 5.30 (s, 2 H), 5.48-5.59 (m, 1 H), 7.10 (d, J = 5.3 Hz, 1 H), 7.14 (d, J = 8.5 Hz, 1 H), 7.33 (dd, J = 8.8, 1.8 Hz, 1 H), 7.84 (d, J = 1.5 Hz, 1 H), 8.30 (d, J = 5.3 Hz, 1 H), 8.66 (s, 1 H) | 0.210 | >100.839 |
| P10 | H | Cl |  |  | C—F | $^1$H NMR (400 MHz, CHLOROFORM-d) δ ppm 0.98-1.04 (m, 2 H), 1.09-1.17 (m, 2 H), 2.19 (m, J = 7.6, 7.6, 7.6, 7.6 Hz, 1 H), 2.87-2.96 (m, 1 H), 2.90 (s, 3 H), 3.08 (t, J = 7.4 Hz, 2 H), 4.49-4.59 (m, 2 H), 5.28 (s, 2 H), 6.81 (m, J = 9.3, 2.0 Hz, 1 H), 7.10 (dd, J = 8.5, 4.5 Hz, 1 H), 7.23-7.35 (m, 3 H), 7.78 (d, J = 1.5 Hz, 1 H) | 0.230 | >9.83603 |

TABLE 1-continued formula (I)

| | $R_1$ | $R_2$ | $R_3$ | $R_4$ | X—$R_5$ | $^1$H NMR | WT activity $EC_{50}$ (nM) | Tox $CC_{50}$ (μM) |
|---|---|---|---|---|---|---|---|---|
| P11 | H | Cl | (CH₂)₄OH | cyclopropyl | C—F | $^1$H NMR (400 MHz, CHLOROFORM-d) δ ppm 0.98-1.04 (m, 2 H), 1.09-1.17 (m, 2 H), 1.59-1.68 (m, 2 H), 1.75 (m, J = 7.5, 7.5, 7.4, 7.2 Hz, 2 H), 2.53 (br. s, 1 H), 2.89 (m, J = 6.9, 3.4, 3.3 Hz, 1 H), 3.69 (t, J = 5.8 Hz, 2 H), 4.30-4.40 (m, 2 H), 5.30 (s, 2 H), 6.76-6.83 (m, 1 H), 7.09 (dd, J = 8.5, 4.3 Hz, 1 H), 7.24 (d, J = 1.3 Hz, 2 H), 7.29 (dd, J = 8.4, 2.4 Hz, 1 H), 7.76 (t, J = 1.1 Hz, 1 H) | 0.253 | >9.83603 |
| P12 | H | Cl | (CH₂)₄OH | cyclopropyl | C—H | $^1$H NMR (400 MHz, CHLOROFORM-d) δ ppm 0.99-1.06 (m, 2 H), 1.10-1.18 (m, 2 H), 1.58-1.67 (m, 2 H), 1.68-1.79 (m, 2 H), 2.59 (br. s., 1 H), 2.91 (m, J = 7.1, 3.5, 3.3 Hz, 1 H), 3.68 (t, J = 5.5 Hz, 2 H), 4.29-4.39 (m, 2 H), 5.31-5.31 (m, 1 H), 5.34 (s, 2 H), 7.08 (m, J = 7.6, 7.4, 7.4, 7.4, 1.4 Hz, 2 H), 7.20 (dd, J = 7.0, 1.8 Hz, 1 H), 7.22-7.25 (m, 2 H), 7.44-7.50 (m, 1 H), 7.76 (s, 1 H) | 0.307 | >9.83603 |
| P13 | H | Cl | (CH₂)₄OH | cyclopropyl | N | $^1$H NMR (400 MHz, DMSO-$d_6$) δ ppm 0.88-0.95 (m, 2 H), 1.04-1.12 (m, 2 H), 1.38-1.49 (m, 2H), 1.59-1.72 (m, 2 H), 2.94-3.03 (m, 1 H), 3.36-3.43 (m, 3 H), 4.34 (t, J = 7.4 Hz, 2 H), 4.55 (t, J = 5.1 Hz, 1 H), 5.39 (s, 2 H), 7.25-7.33 (m, 2 H), 7.62 (d, J = 8.8 Hz, 1 H), 7.66 (d, J = 1.8 Hz, 1 H), 8.25 (d, J = 5.3 Hz, 1 H), 8.37 (s, 1 H) | 0.454 | >9.83603 |
| P14 | H | Br | (CH₂)₄OH | cyclopropyl | N | $^1$H NMR (360 MHz, DMSO-d6) δ ppm 0.92 (m, J = 2.9 Hz, 2 H), 1.07 (m, J = 5.1 Hz, 2 H), 1.37-1.49 (m, 2 H), 1.57-1.71 (m, 2 H), 2.99 (tt, J = 7.0, 3.5 Hz, 1 H), 3.38 (s, 2 H), 4.34 (t, J = 7.5 Hz, 2 H), 4.48 (t, J = 5.1 Hz, 1 H), 5.40 (s, 2 H), 7.29 (d, J = 5.1 Hz, 1 H), 7.39 (dd, J = 8.4, 1.8 Hz, 1 H), 7.59 (d, J = 8.4 Hz, 1 H), 7.81 (d, J = 1.8 Hz, 1 H), 8.25 (d, J = 5.1 Hz, 1 H), 8.37 (s, 1 H) | 0.523 | >98.3603 |
| P15 | H | Cl | isopentyl | cyclopropyl | N | $^1$H NMR (400 MHz, CHLOROFORM-d) δ ppm 0.97 (d, J = 6.6 Hz, 6 H), 1.02 (s, 2 H), 1.13-1.21 (m, 2 H), 1.40-1.50 (m, 2 H), 1.61-1.77 (m, 1 H), 2.91 (s, 1 H), 4.28 (s, 2 H), 5.34 (s, 2 H), 7.13 (dd, J = 5.3, 0.8 Hz, 1 H), 7.22 s, 2 H), 7.75 (dd, J = 1.8, 0.6 Hz, 1 H), 8.33 (d, J = 5.3 Hz, 1 H), 8.63 (d, J = 0.8 Hz, 1 H | <0.620 | >98.3603 |

TABLE 1-continued formula (I)

| | R₁ | R₂ | R₃ | R₄ | X—R₅ | ¹H NMR | WT activity EC₅₀ (nM) | Tox CC₅₀ (μM) |
|---|---|---|---|---|---|---|---|---|
| P16 | H | Br | ~(CH₂)₄OH | cyclopropyl | C—F | ¹H NMR (400 MHz, CHLOROFORM-d) δ ppm 0.96-1.04 (m, 2H), 1.09-1.17 (m, 2 H), 1.59-1.65 (m, 2 H), 1.69-1.80 (m, 2 H), 2.44 (t, J = 5.6 Hz, 1 H), 2.44 (t, J = 5.6 Hz, 1 H), 2.90 (m, J = 6.9, 3.4, 3.3 Hz, 1 H), 3.68 (m, J = 5.6, 5.6, 5.6 Hz, 1 H), 4.34 (m, J = 7.8 Hz, 2H), 5.30 (s, 2 H), 6.80 (ddd, J = 9.5, 8.5, 2.5 Hz, 1 H), 7.09 (dd, J = 8.7, 4.4 Hz, 1 H), 7.20 (d, J = 8.5 Hz, 1 H), 7.29 (dd, J = 8.5, 2.3 Hz, 1 H), 7.37 (dd, J = 8.7, 1.9 Hz, 1 H), 7.93 (d, J = 1.5 Hz, 1 H) | 0.744 | >9.83603 |
| P17 | H | Br | isopentyl | cyclopropyl | N | ¹H NMR (400 MHz, CHLOROFORM-d) δ ppm 0.90 (d, J = 6.5 Hz, 6 H), 0.95 (m, J = 3.5, 1.8, 1.8 Hz, 2 H), 1.10 (d, J = 5.8 Hz, 2 H), 1.32-1.45 (m, 2 H), 1.54-1.68 (m, 1H), 2.84 (spt, J = 3.5 Hz, 1 H), 4.14-4.26 (m, 2 H), 5.27 (s, 2 H), 7.06 (d, J = 5.3 Hz, 1 H), 7.10 (d, J = 8.5 Hz, 1 H), 7.31 (dd, J = 8.5, 1.8 Hz, 1 H), 7.84 (d, J = 1.8 Hz, 1 H), 8.26 (d, J = 5.3 Hz, 1 H), 8.55 (s, 1 H) | 0.808 | >49.1802 |
| P18 | H | Br | ~(CH₂)₄OAc | cyclopropyl | N | ¹H NMR (400 MHz, CHLOROFORM-d) δ ppm 0.98-1.05 (m, 2 H), 1.14-1.21 (m, 2 H), 1.60-1.79 (m, 4 H), 2.01 (s, 3 H), 2.89-2.97 (m, 1 H), 4.04 (t, J = 6.1 Hz, 2 H), 4.34 (t, J = 7.1 Hz, 2 H), 5.35 (s, 2 H), 7.13 (dd, J = 5.3, 0.8 Hz, 1 H), 7.19 (d, J = 8.8 Hz, 1 H), 7.39 dd (J = 8.6, 1.8 Hz, 1 H), 7.92 (d, J = 1.6 Hz, 1 H), 8.34 (d, J = 5.3 Hz, 1 H), 8.68 (s, 1 H) | 1.07 | >100.839 |
| P19 | H | Cl | ~(CH₂)₄OC(O)C(CH₃)₃ | cyclopropyl | C—H | ¹H NMR (400 MHz, CHLOROFORM-d) δ ppm 0.98-1.05 (m, 2 H), 1.11-1.20 (m, 2 H), 1.15 (s, 9 H), 1.62-1.69 (m, 4 H), 2.90 (m, J = 7.0, 3.4, 3.4 Hz, 1 H), 3.97-4.04 (m, 2 H), 4.37 (t, J = 6.9 Hz, 2 H), 5.33 (s, 2 H), 7.01-7.12 (m, 2 H), 7.17-7.21 (m, 1 H), 7.22-7.24 (m, 2 H), 7.40-7.45 (m, 1 H), 7.74-7.78 (m, 1 H) | 2.59 | >9.83603 |
| P20 | H | Cl | ~(CH₂)₄OC(O)C(CH₃)₃ | cyclopropyl | C—F | ¹H NMR (400 MHz, CHLOROFORM-d) δ ppm 0.91-1.04 (m, 2 H), 1.10-1.19 (m, 2 H), 1.10-1.19 (m, 2 H), 1.15 (s, 9 H), 1.57-1.74 (m, 4 H), 2.90 (m, J = 6.9, 3.4, 3.3 Hz, 1 H), 4.02 (t, J = 6.0 Hz, 2 H), 4.37 (t, J = 7.0 Hz, 2 H), 5.29 (s, 2 H), 6.79 (ddd, J = 9.6, 8.6, 2.4 Hz, 1 H), 7.08 (dd, J = 8.5, 4.3 Hz, 1 H), 7.20-7.38 (m, 4 H), 7.77 (t, J = 1.1 Hz, 1 H) | 4.09 | >9.83603 |

TABLE 1-continued formula (I)

| | R1 | R2 | R3 | R4 | X—R5 | 1H NMR | WT activity EC50 (nM) | Tox CC50 (μM) |
|---|---|---|---|---|---|---|---|---|
| P21 | H | Br | (CH2)3-N(CH3)2 | cyclopropyl | N | 1H NMR (400 MHz, CHLOROFORM-d) δ ppm 0.95 (m, J = 3.5 Hz, 2 H), 1.09 (m, J = 5.8 Hz, 2 H), 1.79 (m, J = 6.7 Hz, 2 H), 2.04-2.14 (m, 8 H), 2.85 (spt, J = 3.6 Hz, 1 H), 4.33 (t, J = 6.8 Hz, 2 H), 5.37 (s, 2 H), 7.05 (d, J = 5.3 Hz, 1 H), 7.20 (d, J = 8.3 Hz, 1 H), 7.30 (dd, J = 8.3, 1.6 Hz, 1 H), 7.82 (d, J = 1.5 Hz, 1 H), 8.26 (d, J = 5.3 Hz, 1 H), 8.60 (s, 1 H) | 4.12 | >98.3603 |
| P22 | H | Br | (CH2)4-OC(O)CH3 | cyclopropyl | C—F | 1H NMR (400 MHz, CHLOROFORM-d) δ ppm 1.01 (m, J = 3.6, 1.9, 1.9 Hz, 2 H), 1,13 (m, J = 7.4, 1.6 Hz, 2 H), 1.59-1.73 (m, 4 H), 2.00 (s, 3 H), 2.89 (m, J = 6.9, 6.9, 3.8, 3.5 Hz, 1 H), 4.01 (t, J = 6.0 Hz, 2 H), 4.35 (t, J = 7.0 Hz, 2 H), 5.29 (s, 2 H), 6.79 (td, J = 9.2, 2.5 Hz, 1 H), 7.08 (dd, J = 8.7, 4.4 Hz, 1 H), 7.19 (d, J = 8.5 Hz, 1 H), 7.24 (dd, J = 8.5, 2.5 Hz, 1 H), 7.38 (dd, J = 8.7, 1.9 Hz, 1 H), 7.93 (d, J = 1.8 Hz, 1 H) | <0.810 | >9.83603 |
| P23 | H | Br | (CH2)4-F | cyclopropyl | C—F | 1H NMR (400 MHz, CHLOROFORM-d) δ ppm 0.96-1.04 (m, 2 H), 1.10-1.18 (m, 2 H), 1.65-1.83 (m, 4 H), 2.88 (m, J = 6.9, 3.4, 3.3 Hz, 1 H), 4.31-4.39 (m, 3H), 4.47 (t, J = 5.3 Hz, 1 H), 5.30 (s, 2 H), 6.79 (ddd, J = 9.5, 8.7, 2.4 Hz, 1H), 7.08 (dd, J = 8.7, 4.4 Hz, 1 H), 7.17-7.25 (m, 2 H), 7.38 (dd, J = 8.5, 1.8 Hz, 1 H), 7.93 (d, J = 1.8 Hz, 1 H) | <1.6 | >9.83603 |
| P24 | H | Cl | (CH2)3-SO2CH3 | cyclopropyl | C—H | 1H NMR (400 MHz, DMSO-d6) δ ppm 0.85-0.96 (m, 2 H), 1.05 (m, J = 5.3 Hz, 2 H), 2.08 (dt, J = 14.4, 7.2 Hz, 2 H), 2.88-3.02 (m, 4 H), 3.20 (s, 2 H), 4.48 (t, J = 7.3 Hz, 2 H), 5.35 (s, 2 H), 6.96-7.15 (m, 2 H), 7.19-7.27 (m, 2 H), 7.30 (dd, J = 8.8,1.3 Hz, 1 H), 7.59-7.76 (m, 2 H) | <0.150 | >9.83603 |
| P25 | H | Cl | (CH2)4-F | cyclopropyl | C—H | 1H NMR (400 MHz, CHLOROFORM-d) δ ppm 0.99-1.05 (m, 2 H), 1.11-1.17 (m, 2 H), 1.65-1.81 (m, 4 H), 2.86-2.94 (m, 1 H), 4.36 (m, J = 5.8 Hz, 2 H), 4.46 (t, J = 5.4 Hz, 1 H), 5.34 (s, 2 H), 7.02-7.12 (m, 2 H), 7.17-7.22 (m, 1 H), 7.22-7.25 (m, 2 H), 7.38-7.43 (m, 1 H), 7.76 (m, J = 1.5 Hz, 1 H | <0.150 | >9.83603 |
| P26 | H | Cl | (CH2)4-CN | cyclopropyl | N | 1H NMR (400 MHz, CHLOROFORM-d) δ ppm 0.97-1.04 (m, 2 H), 1.14-1.22 (m, 2 H), 2.02-2.12 (m, 2 H), 2.47 (t, J = 7.2 Hz, 2 H), 2.93 (m, J = 7.0, 3.4, 3.4 Hz, 1 H), 4.44-4.52 (m, 2 H), 5.33 (s, 2 H), 7.14 (dd, J = 5.3, 0.8 Hz, 1 H), 7.25-7.30 (m, 1 H), 7.75 (t, J = 1.3 Hz, 1 H), 8.34 (d, J = 5.3 Hz, 1 H), 8.72 (d, J = 0.5 Hz, 1 H) | <0.150 | >9.83603 |

TABLE 1-continued formula (I)

|  | R₁ | R₂ | R₃ | R₄ | X—R₅ | ¹H NMR | WT activity EC₅₀ (nM) | Tox CC₅₀ (μM) |
|---|---|---|---|---|---|---|---|---|
| P27 | H | Br | (CH₂)₃CN | cyclopropyl | N | ¹H NMR (400 MHz, CHLOROFORM-d) δ ppm 0.97-1.04 (m, 2 H), 1.13-1.22 (m, 2 H), 2.01-2.13 (m, 2 H), 2.47 (t, J = 7.2 Hz, 2 H), 2.93 (m, J = 7.0, 3.4, 3.4 Hz, 1 H), 4.42-454 (m, 2 H), 4.42-4.54 (m, 2 H), 5.34 (s, 2 H), 7.14 (dd, J = 5.3, 0.8 Hz, 1 H), 7.25 (d, J = 1.0 Hz, 1 H), 7.42 (dd, J = 8.7, 1.9 Hz, 1 H), 7.92 (d, J = 1.8 Hz, 1 H), 8.35 (d, J = 5.3 Hz, 1 H), 8.73 (d, J = 0.8 Hz, 1 H) | <0.150 | >9.83603 |

TABLE 2 formula (I)

|  | R₁ | R₂ | R₃ | R₄ | X—R₅ | ¹H NMR | WT activity EC₅₀ (nM) | SI CC₅₀/EC50 |
|---|---|---|---|---|---|---|---|---|
| P28 | H | Cl | isopentyl | cyclopropyl | C—F | ¹H NMR (400 MHz, CHLOROFORM-d) δ ppm 0.95 (d, J = 6.5 Hz, 6 H), 0.98-1.05 (m, 2 H), 1.13-1.2 (m, 2 H), 1.35-1.46 (m, 2 H), 1.67-1.7 (m, 1 H), 2.87-1.9 (m, 1 H), 4.24-4.32 (m, 2 H), 5.29 (s, 2 H), 6.74-6.83 (m, 1 H), 7.07 (dd, J = 8.7, 4.4 Hz, 1 H), 7.15-7.26 (m, 3 H), 7.76 (d, J = 1.8 Hz, 1 H) | 2.32 | 14563 |
| P29 | H | Cl | (CH₂)₃CN | isopropenyl | N |  | 0.08 | >1 240 820 |

TABLE 2-continued formula (I)

|  | R₁ | R₂ | R₃ | R₄ | X—R₅ | ¹H NMR | WT activity EC₅₀ (nM) | SI CC₅₀/EC50 |
|---|---|---|---|---|---|---|---|---|
| P30 | H | Cl | (CH₂)₄F | isopropenyl | N | | 0.09 | 1 000 000 |
| P31 | H | Cl | (CH₂)₄F | cyclopropyl | N | | 0.19 | >267110 |
| P32 | H | Br | isopentyl | cyclopropyl | C—F | ¹H NMR (400 MHz, CHLOROFORM-d) δ ppm 0.95 (d, J = 6.8 Hz, 6 H), 1.10-1.18 (m, 2 H), 1.35-1.45 (m, 2 H), 1.68-1.7 (m, 2 H), 2.87-2.9 (m, 1 H), 4.25-4.32 (m, 2 H), 5.29 (s, 2 H), 6.74-6.82 (m, 1 H), 7.07 (dd, J = 8.5, 4.5 Hz, 1 H), 7.14-7.21 (m, 2 H), 7.37 (dd, J = 8.5, 1.8 Hz, 1 H), 7.92 (d, J = 1.5 Hz, 1 H) | 2.53 | 25508 |
| P33 | H | Cl | (CH₂)₄F | tert-butyl isovalerate | N | ¹H NMR (400 MHz, CHLOROFORM-d) δ ppm 1.48 (s, 9 H) 1.66-1.79 (m, 4 H) 4.29 (t, J = 7.28 Hz, 2 H) 4.37 (t, J = 5.14 Hz, 1 H) 4.46-4.51 (m, 1 H) 4.54 (s, 2 H) 5.41 (s, 2 H) 6.83 (d, J = 5.27 Hz, 1 H) 7.23-7.25 (m, 2 H) 7.76 (br. s, 1 H) 8.32 (d, J = 5.52 Hz, 1 H) 8.66 (s, 1 H) | 1.9 | >49120 |
| P34 | H | Cl | (CH₂)₄F | isopropyl sulfonyl | N | | 0.09 | >1 048 580 |

TABLE 2-continued formula (I)

| | $R_1$ | $R_2$ | $R_3$ | $R_4$ | X—$R_5$ | $^1$H NMR | WT activity $EC_{50}$ (nM) | SI $CC_{50}/EC_{50}$ |
|---|---|---|---|---|---|---|---|---|
| P35 | H | Cl | isohexyl | cyclopropyl | CH | $^1$H NMR (400 MHz, CHLOROFORM-d) δ ppm 0.94 (d, J = 6.8 Hz, 6H), 0.99-1.06 (m, 2 H), 1.10-1.18 (m, 2 H), 1.33-1.44 (m, 2 H), 1.60-1.73 (m, 1 H), 2.83-2.93 (m, 1 H), 4.24-4.34 (m, 2 H), 5.33 (s, 2 H), 6.99-7.12 (m, 2 H), 7.15-7.25 (m, 3 H), 7.36 (d, J = 7.3 Hz, 1 H), 7.75 (d, J = 1.3 Hz, 1 H) | 2.63 | 33466 |
| P36 | H | Br | -(CH2)3-COOH | cyclopropyl | N | 1H NMR (400 MHz, DMSO-d) δ ppm 1.02 (s, 2 H) 1.13 (s, 2 H) 2.03 (s, 2 H) 2.41 (s, 2 H) 3.14 (s, 1 H) 4.43 (s, 2 H) 5.67 (s, 2 H) 7.54 (s, 1 H) 7.71-7.90 (b, 3 H) 8.53-8.72 (b, 1) 8.80-8.99 (b, 1 H) | nd | nd |
| P37 | H | Cl | -(CH2)4-F | -C(CH3)(CF3)- | N | 1H NMR (400 MHz, CHLOROFORM-d) δ ppm 1.67-1.84 (m, 4 H) 4.32 (t, J = 7.40 Hz, 2 H) 4.38 (t, J = 5.14 Hz, 1 H) 4.44-4.55 (m, 3 H) 5.42 (s, 2 H) 7.02 (d, J = 5.27 Hz, 1 H) 7.21-7.31 (m, 2 H) 7.76 (d, J = 1.00 Hz, 1 H) 8.39 (d, J = 5.52 Hz, 1 H) 8.76 (s, 1 H) | 0.26 | >387686 |
| P38 | H | Br | -(CH2)3-C(O)NH-(CH2)2-SO2-imidazole | cyclopropyl | N | $^1$H NMR (400 MHz, DMSO-$d_6$) δ ppm 0.88-0.96 (m, 2 H), 1.02-1.12 (m, 2 H), 1.77-1.91 (m, 2 H), 2.09 (t, J = 6.9 Hz, 2 H), 2.95-3.05 (m, 1 H), 3.22-3.53 (m, 2 H), 3.88 (t, J = 6.0 Hz, 2 H), 4.31 (t, J = 7.3 Hz, 2 H), 5.40 (s, 2 H), 7.16 (s, 1 H), 7.30 (d, J = 5.3 Hz, 1 H), 7.41 (d, J = 8.5 Hz, 1 H), 7.59 (d, J = 8.5 Hz, 1 H), 7.66 (s, 1 H), 7.79 (s, 1 H), 8.08 (t, J = 5.3 Hz, 1 H), 8.17 (s, 1 H), 8.26 (d, J = 5.3 Hz, 1 H), 8.39 (s, 1 H) | 0.22 | >445390 |
| P39 | H | Cl | -(CH2)4-O-C(O)-C(CH3)3 | -C(CH3)2-SO2-CH3 | N | 1H NMR (400 MHz, CHLOROFORM-d) δ ppm 1.17 (s, 9 H) 1.67-1.89 (m, 4 H) 3.56 (s, 3 H) 4.09 (t, J = 6.02 Hz, 2 H) 4.34 (t, J = 7.50 Hz, 2 H) 5.36 (s, 2 H) 7.24-7.30 (m, 3 H) 7.68 (dd, J = 5.40, 0.88 Hz, 1 H) 7.72-7.77 (m, 1 H) 8.43 (d, J = 5.52 Hz, 1 H) 8.86 (d, J = 0.50 Hz, 1 H) | 0.27 | 124761 |

TABLE 2-continued formula (I)

| | R₁ | R₂ | R₃ | R₄ | X—R₅ | ¹H NMR | WT activity EC₅₀ (nM) | SI CC₅₀/EC50 |
|---|---|---|---|---|---|---|---|---|
| P40 | H | Cl | (pentyl-F chain) | (3,3-difluoroisobutyl) | N | 1H NMR (400 MHz, CHLOROFORM-d) δ ppm 1.67-1.85 (m, 4 H) 4.19-4.35 (m, 4 H) 4.38 (t, J = 5.27 Hz, 1 H) 4.50 (t, J = 5.14 Hz, 1 H) 5.41 (s, 2 H) 6.07 (tt, J = 55.00, 3.80 Hz, 1 H) 7.03 (d, J = 5.27 Hz, 1 H) 7.24-7.26 (m, 2 H) 7.71-7.81 (m, 1 H) 8.37 (d, J = 5.27 Hz, 1 H) 8.72 (s, 1 H) | 0.048 | 2000000 |
| P41 | H | Cl | (pentyl-F chain) | (4-fluorobenzyl) | N | 1H NMR (400 MHz, DMSO-d6) δ ppm 1.60-1.82 (m, 4 H) 4.33-4.43 (m, 3 H) 4.46-4.52 (m, 1 H) 5.12 (s, 2 H) 5.49 (s, 2 H) 7.15-7.22 (m, 2 H) 7.26-7.33 (m, 2 H) 7.39-7.46 (m, 2 H) 7.65 (d, J = 5.77 Hz, 1 H) 7.66 (s, 1 H) 8.21 (d, J = 5.27 Hz, 1 H) 8.42 (s, 1 H) | 0.16 | 503466 |
| P42 | H | Cl | (pentyl-F chain) | (CH₂C(O)NH₂ isobutyl) | N | 1H NMR (400 MHz, DMSO-d6) δ ppm 1.61-1.80 (m, 4 H) 4.34-4.42 (m, 3 H) 4.49-4.52 (m, 1 H) 4.53 (s, 2 H) 5.45 (s, 2 H) 7.21 (m, J = 4.77 Hz, 1 H) 7.29 (dd, J = 8.78, 2.01 Hz, 1 H) 7.31-7.34 (m, 1 H) 7.65 (d, J = 8.78 Hz, 1 H) 7.67-7.71 (m, 2 H) 8.22 (d, J = 5.27 Hz, 1 H) 8.43 (s, 1 H) | 1.68 | >59490 |
| P43 | H | Cl | (pentyl-F chain) | (methylsulfonyl isobutyl) | N | 1H NMR (400 MHz, DMSO-d6) δ ppm 1.43-1.54 (m, 2 H) 1.72-1.83 (m, 2 H) 3.40-3.47 (m, 2 H) 3.71 (s, 3 H) 4.33-4.41 (m, 2 H) 4.48 (t, J = 5.02 Hz, 2 H) 5.49 (s, 2 H) 7.30 (dd, J = 8.80, 1.80 Hz, 1 H) 7.62 (d, J = 5.27 Hz, 1 H) 7.65 (d, J = 6.27 Hz, 1 H) 7.67 (s, 1 H) 8.37 (d, J = 5.52 Hz, 1 H) 8.61 (s, 1 H) | 0.078 | >1285610 |
| P44 | H | Cl | (butyl-NH-pyrimidin-2-yl chain) | (cyclopropyl) | N | 1H NMR (400 MHz, DMSO-d6) δ ppm 0.87-0.94 (m, 2 H) 1.02-1.09 (m, 2 H) 1.93-2.04 (m, 2 H) 2.95-3.04 (m, 1 H) 3.25-3.30 (m, 2 H) 4.43 (t, J = 7.28 Hz, 2 H) 5.40 (s, 2 H) 6.54-6.59 (m, 1 H) 7.22-7.32 (m, 3 H) 7.63 (d, J = 8.78 Hz, 1 H) 7.65 (d, J = 2.01 Hz, 1 H) 8.25 (d, J = 4.77 Hz, 2 H) 8.23-8.28 (m, 1 H) 8.37 (s, 1 H) | 0.3 | 302162 |

TABLE 2-continued formula (I)

|  | R₁ | R₂ | R₃ | R₄ | X—R₅ | ¹H NMR | WT activity EC₅₀ (nM) | SI CC₅₀/ EC50 |
|---|---|---|---|---|---|---|---|---|
| P45 | H | Cl | (CH₂)₃COOH | cyclopropyl | N | ¹H NMR (400 MHz, DMSO-d₆) δ ppm 0.87-0.94 (m, 2 H), 1.02-1.08 (m, 2 H), 1.76-1.88 (m, 2 H), 2.11 (t, J = 6.9 Hz, 2 H), 2.99 (m, 1 H), 4.33 (t, J = 7.7 Hz, 2 H), 5.42 (s, 2 H), 7.25 (d, J = 2.0 Hz, 1 H), 7.26-7.31 (m, 1 H), 7.63 (d, J = 1.8 Hz, 1 H), 7.68 (d, J = 8.5 Hz, 1 H), 8.25 (d, J = 5.0 Hz, 1 H), 8.38 (s, 1 H) | C. 5.15 | D. >19412 |
| P46 | H | Cl | (CH₂)₄-phthalimide | cyclopropyl | N | ¹H NMR (400 MHz, CHLOROFORM-d) δ ppm 0.94-1.06 (m, 2 H) 1.14-1.22 (m, 2 H) 1.66-1.76 (m, 4 H) 2.92-3.03 (m, 1 H) 3.64-3.72 (m, 2 H) 4.33-4.42 (m, 2 H) 5.38 (s, 2 H) 7.10 (dd, J = 5.27, 0.50 Hz, 1 H) 7.22 (dd, J = 8.78, 1.76 Hz, 1 H) 7.27-7.30 (m, 1 H) 7.71-7.76 (m, 3 H) 7.81-7.86 (m, 2 H) 8.29 (d, J = 5.27 Hz, 1 H) 8.67 (s, 1 H) | 0.57 | >44185 |
| P47 | H | Cl | (CH₂)₄-(2-pyridyl) | cyclopropyl | N | 1H NMR (400 MHz, DMSO-d6) δ ppm 0.86-0.95 (m, 2 H) 1.03-1.11 (m, 2 H) 1.61-1.75 (m, 4 H) 2.68-2.77 (m, 2 H) 2.94-3.02 (m, 1 H) 4.32-4.43 (m, 2 H) 5.39 (s, 2 H) 7.15-7.22 (m, 2 H) 7.24-7.31 (m, 2 H) 7.62 (d, J = 8.53 Hz, 1 H) 7.64-7.71 (m, 2 H) 8.24 (d, J = 5.27 Hz, 1 H) 8.37 (s,1 H) 8.45 (d, J = 4.27 Hz, 1 H) | 0.76 | 84254 |
| P48 | H | Br | (CH₂)₃C(O)-morpholine | cyclopropyl | N | ¹H NMR (400 MHz, DMSO-d₆) δ ppm 0.86-0.95 (m, 2 H), 1.03-1.12 (m, 2 H), 1.90 (tdd, J = 7.3, 7.3, 7.2, 6.9 Hz, 2 H), 2.39 (t, J = 6.9 Hz, 2 H), 2.95-3.04 (m, 1 H), 3.40 (dt, J = 17.9, 4.5 Hz, 4 H), 3.48-3.61 (m, 4 H), 4.36 (t, J = 7.5 Hz, 2 H), 5.42 (s, 2 H), 7.28 (d, J = 5.3 Hz, 1 H), 7.41 (dd, J = 8.5, 1.8 Hz, 1 H), 7.63 (d, J = 8.8 Hz, 1 H), 7.79 (d, J = 1.8 Hz, 1 H), 8.26 (d, J = 5.0 Hz, 1 H), 8.40 (s, 1 H) | 0.97 | >102584 |

TABLE 2-continued formula (I)

| | R₁ | R₂ | R₃ | R₄ | X—R₅ | ¹H NMR | WT activity EC₅₀ (nM) | SI CC₅₀/EC50 |
|---|---|---|---|---|---|---|---|---|
| P49 | H | Cl | (alkyl chain with C(=O)NH-S(=O)₂-cyclopropyl) | cyclopropyl | N | ¹H NMR (400 MHz, DMSO-d₆) δ ppm 0.70-0.77 (m, 2 H), 0.80-0.87 (m, 2 H), 0.89-0.96 (m, 2 H), 1.02-1.10 (m, 3 H), 1.76-1.89 (m, 2 H), 2.13 (t, J = 6.9 Hz, 2 H), 2.76-2.86 (m, 1 H), 3.01 (m, 1 H), 3.29 (dt, J = 13.0, 6.5 Hz, 1 H), 4.33 (m, 1 H), 5.42 (s, 1 H), 7.18 (dd, J = 8.5, 2.0 Hz, 1 H), 7.28 (dd, J = 5.3, 0.5 Hz, 1 H), 7.56 (d, J = 8.5 Hz, 1 H), 7.80 (d, J = 1.8 Hz, 1 H), 7.85-8.19 (m, 1 H), 8.25 (d, J = 5.3 Hz, 1 H), 8.38 (s, 1 H) | 1.8 | >55412 |
| P50 | H | Cl | (propyl-phenyl) | cyclopropyl | N | ¹H NMR (400 MHz, CHLOROFORM-d) δ ppm 0.94-1.03 (m, 2 H) 1.12-1.20 (m, 2 H) 1.90-2.01 (m, 2 H) 2.65 (t, J = 8.00 Hz, 2 H) 2.85-2.93 (m, 1 H) 4.35 (t, J = 7.50 Hz, 2 H) 5.32 (s, 2 H) 7.06-7.13 (m, 4 H) 7.19-7.24 (m, 2 H) 7.27-7.31 (m, 2 H) 7.75 (d, J = 2.01 Hz, 1 H) 8.34 (d, J = 5.27 Hz, 1 H) 8.67 (d, J = 0.50 Hz, 1 H) | 0.23 | 93799 |
| P51 | H | Cl | (propyl-imidazolyl) | cyclopropyl | N | ¹H NMR (400 MHz, CHLOROFORM-d) δ ppm 0.92-1.05 (m, 2 H) 1.11-1.26 (m, 2 H) 2.09-2.30 (m, 2 H) 2.79-3.03 (m, 1 H) 4.08 (t, J = 7.03 Hz, 2 H) 4.25-4.46 (m, 2 H) 5.28 (s, 2 H) 6.94 (t, J = 1.25 Hz, 1 H) 7.03 (d, J = 8.53 Hz, 1 H) 7.10-7.15 (m, 2 H) 7.23 (dd, J = 8.66, 1.88 Hz, 1 H) 7.50 (s, 1 H) 7.75 (d, J = 1.76 Hz, 1 H) 8.34 (d, J = 5.27 Hz, 1 H) 8.73 (d, J = 0.50 Hz, 1 H) | 0.25 | >401504 |
| P52 | H | Cl | (alkyl-C(=O)O-tBu) | cyclopropyl | N | ¹H NMR (360 MHz, DMSO-d₆) δ ppm 0.85-0.96 (m, 2 H), 1.02-1.11 (m, 2 H), 1.35 (s, 9 H), 1.86 (s, 2 H), 2.29 (t, J = 7.3 Hz, 2 H), 2.99 (tt, J = 7.0, 3.5 Hz, 1 H), 4.34 (t, J = 7.5 Hz, 2 H), 5.40 (s, 2 H), 7.25-7.34 (m, 2 H), 7.59-7.70 (m, 2 H), 8.26 (d, J = 5.1 Hz, 1 H), 8.40 (s, 1 H) | 0.55 | 70937 |
| P53 | H | Cl | (alkyl-S(=O)₂-CH₃) | CH₂-CF₃ (trifluoropropyl) | C—F | ¹H NMR (400 MHz, DMSO-d₆) δ ppm 2.17 (m, J = 7.03 Hz, 2 H) 3.01 (s, 3 H) 3.21-3.28 (m, 2 H) 4.49 (t, J = 7.28 Hz, 2 H) 4.85 (q, J = 9.29 Hz, 2 H) 5.46 (s, 2 H) 6.94-7.04 (m, 1 H) 7.23-7.29 (m, 1 H) 7.31 (m, J = 8.50 Hz, 1 H) 7.33-7.41 (m, 1 H) 7.64-7.67 (m, 1 H) 7.69 (d, J = 8.78 Hz, 1 H) | 0.221 | 77253 |

TABLE 2-continued formula (I)

| | R₁ | R₂ | R₃ | R₄ | X—R₅ | ¹H NMR | WT activity EC₅₀ (nM) | SI CC₅₀/EC50 |
|---|---|---|---|---|---|---|---|---|
| P54 | H | Cl | (CH₂)₃C(O)O-tBu chain | cyclopropyl | N | 1H NMR (400 MHz, DMSO-d6) δ ppm 0.85-0.94 (m, 2 H) 1.01-1.15 (m, 2 H) 1.81-1.99 (m, 2 H) 2.26-2.45 (m, 2 H) 2.90-3.06 (m, 1 H) 4.34-4.54 (m, 2 H) 5.41 (s, 2 H) 7.24-7.36 (m, 2 H) 7.66-7.72 (m, 2 H) 8.26 (d, J = 5.27 Hz, 1 H) 8.42 (s, 1 H) | 0.072 | >1391750 |
| P55 | H | Cl | (CH₂)₃CF₃ chain | CH₂C(CH₃)(F)CF₃ | N | 1H NMR (400 MHz, DMSO-d6) δ ppm 1.87-2.04 (m, 2 H) 2.28-2.46 (m, 2 H) 4.35-4.55 (m, 2 H) 4.78-5.01 (m, 2 H) 5.52 (s, 2 H) 7.31 (d, J = 8.28 Hz, 1 H) 7.44 (d, J = 5.27 Hz, 1 H) 7.64-7.67 (m, 1 H) 7.70 (d, J = 8.53 Hz, 1 H) 8.33 (d, J = 5.27 Hz, 1 H) 8.50 (s, 1 H) | 0.024 | 2000000 |
| P56 | H | Cl | (CH₂)₄F chain | CH₂C(CH₃)(F)CF₃ | C—F | ¹H NMR (360 MHz, DMSO-d₆) δ ppm 1.61-1.85 (m, 4 H), 4.31-4.58 (m, 4 H), 4.87 (q, J = 9.1 Hz, 2 H), 5.45 (s, 2 H), 6.92-7.06 (m, 1 H), 7.21-7.32 (m, 2 H), 7.36 (dd, J = 8.8, 4.4 Hz, 1 H), 7.61-7.72 (m, 2 H) | 1.71 | >58644 |
| P57 | H | Cl | (CH₂)₃CF₃ chain | CH₂C(CH₃)(F)CF₃ | C—F | 1H NMR (400 MHz, DMSO-d6) δ ppm 1.81-2.03 (m, 2 H) 2.27-2.44 (m, 2 H) 4.43 (t, J = 7.53 Hz, 2 H) 4.85 (q, J = 9.29 Hz, 2 H) 5.45 (s, 2 H) 6.91-7.07 (m, 1 H) 7.27 (dd, J = 9.03. 2.51 Hz, 1 H) 7.31 (dd, J = 8.78, 2.01 Hz, 1 H) 7.35 (dd, J = 8.66, 4.39 Hz, 1 H) 7.67 (d, J = 2.01 Hz, 1 H) 7.69 (d, J = 8.78 Hz, 1 H) | 1.1 | 92032 |
| P58 | H | Cl | (CH₂)₃CF₃ chain | cyclopropyl | C—F | 1H NMR (400 MHz, DMSO-d6) δ ppm 0.85-0.91 (m, 2 H) 1.02-1.08 (m, 2 H) 1.82-1.93 (m, 2 H) 2.30-2.43 (m, 2 H) 2.88-2.95 (m, 1 H) 4.42 (t, J = 7.65 Hz, 2 H) 5.35 (s, 2 H) 6.89-6.96 (m, 1 H) 7.17 (dd, J = 9.03, 2.51 (Hz, 1 H) 7.22 (dd, J = 8.53, 4.52 Hz, 1 H) 7.30 (dd, J = 8.66, 1.88 Hz, 1 H) 7.66-7.70 (m, 2 H) | 0.49 | 104559 |

TABLE 2-continued formula (I)

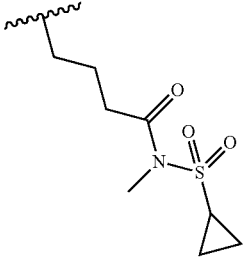 [SMILES: *CCCC(=O)N(C)S(=O)(=O)C1CC1]

| | R₁ | R₂ | R₃ | R₄ | X—R₅ | ¹H NMR | WT activity EC₅₀ (nM) | SI CC₅₀/EC50 |
|---|---|---|---|---|---|---|---|---|
| P59 | H | Cl | 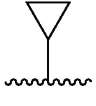 | 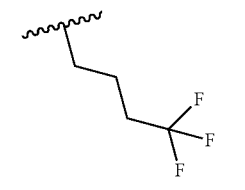 [SMILES: *CCCC(F)(F)F] | N | ¹H NMR (400 MHz, DMSO-d₆) δ ppm 0.87-0.94 (m, 2 H), 1.01-1.15 (m, 6 H), 1.89-2.00 (m, 2 H), 2.82 (t, J = 7.0 Hz, 2 H), 2.94-3.02 (m, 1 H), 3.14-3.20 (m, 1 H), 3.17 (s, 3 H), 4.38 (t, J = 7.7 Hz, 2 H), 5.42 (s, 2 H), 7.26-7.33 (m, 2 H), 7.64-7.69 (m, 2 H), 8.26 (d, J = 5.3 Hz, 1 H), 8.40 (br. s., 1 H) | 0.17 | >604770 |
| P60 | H | Cl | 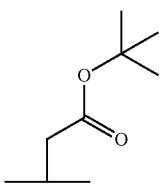 | 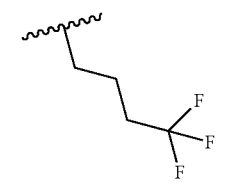 [SMILES: *CCCC(F)(F)F] | N | ¹H NMR (400 MHz, CHLOROFORM-d) δ ppm 1.48 (s, 9 H), 1.79-1.90 (m, 2 H), 2.09-2.26 (m, 2 H), 4.27-4.38 (m, 2 H), 4.53 (s, 2 H), 5.41 (s, 2 H), 6.84 (d, J = 5.3 Hz, 1 H), 7.19-7.24 (m, 1 H), 7.25-7.31 (m, 1 H), 7.78 (d, J = 1.8 Hz, 1 H), 8.34 (d, J = 5.5 Hz, 1 H), 8.68 (s, 1 H) | 1.68 | >59486 |
| P61 | H | Cl | 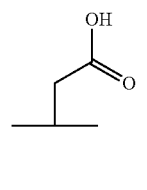 | 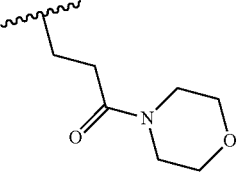 [SMILES: *CCC(=O)N1CCOCC1] | N | ¹H NMR (400 MHz, DMSO-d₆) δ ppm 1.84-2.01 (m, 2 H), 2.30-2.47 (m, 2 H), 4.34-4.59 (m, 4 H), 5.48 (s, 2 H), 7.24 (br. s., 1 H), 7.31 (dd, J = 8.7, 1.6 Hz, 1 H), 7.67 (d, J = 1.3 Hz, 1 H), 7.69 (d, J = 8.5 Hz, 1 H), 8.22 (d, J = 5.3 Hz, 1 H), 8.41 (s, 1 H) | 10 | >9874 |
| P62 | H | Cl | 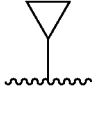 | 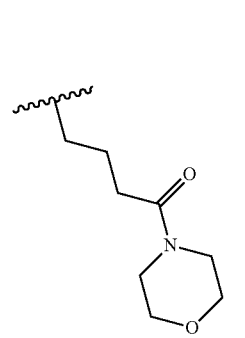 [SMILES: *CCCC(=O)N1CCOCC1] | C—F | ¹H NMR (360 MHz, DMSO-d₆) δ ppm 0.86-0.92 (m, 2 H), 1.01-1.08 (m, 2 H), 2.87 (t, J = 6.8 Hz, 2 H), 2.94 (tt, J = 6.9, 3.6 Hz, 1 H), 3.24-3.31 (m, 2 H), 3.35-3.43 (m, 4 H), 3.43-3.49 (m, 2 H), 4.58 (t, J = 6.8 Hz, 2 H), 5.46 (s, 2 H), 6.91 (ddd, J = 10.2, 8.6, 2.6 Hz, 1 H), 7.13 (dd, J = 9.1, 2.5 Hz, 1 H), 7.21 (dd, J = 8.6, 4.6 Hz, 1 H), 7.26 (dd, J = 8.6, 2.0 Hz, 1 H), 7.64 (d, J = 8.6 Hz, 1 H), 7.64 (d, J = 2.0 Hz, 1 H) | 1.36 | >73334 |
| P63 | H | Cl |  | 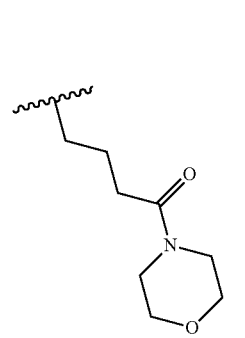 [SMILES: *CCCC(=O)N1CCOCC1] | N | ¹H NMR (360 MHz, DMSO-d₆) δ ppm 0.88-0.93 (m, 2 H), 1.03-1.10 (m, 2 H), 1.85-1.94 (m, 2 H), 2.39 (t, J = 7.0 Hz, 2 H), 2.99 (tt, J = 7.0, 3.6 Hz, 1 H), 3.35-3.45 (m, 4 H), 3.48-3.56 (m, 4 H), 4.35 (t, J = 7.7 Hz, 2 H), 5.42 (s, 2 H), 7.28-7.32 (m, 2 H), 7.63-7.71 (m, 2 H), 8.26 (d, J = 5.1 Hz, 1 H), 8.40 (s, 1 H) | 1 | >98994 |

TABLE 2-continued formula (I)

| | R₁ | R₂ | R₃ | R₄ | X—R₅ | ¹H NMR | WT activity EC₅₀ (nM) | SI CC₅₀/EC50 |
|---|---|---|---|---|---|---|---|---|
| P64 | H | Cl | (4-morpholinyl-carbonyl)propyl | cyclopropyl | N | ¹H NMR (360 MHz, DMSO-d₆) δ ppm 0.91 (m, J = 2.93 Hz, 2 H), 1.07 (s, 2 H) 2.88 (t, J = 6.59 Hz, 2 H) 2.99 (tt, J = 6.95, 3.48 Hz, 1 H) 3.30 (m, J = 4.80 Hz, 2 H) 3.37-3.50 (m, 6 H) 4.59 (t, J = 6.59 Hz, 2 H) 5.52 (s, 2 H) 7.27 (s, 2 H) 7.58-7.71 (m, 2 H) 8.24 (d, J = 5.12 Hz, 1 H) 8.37 (s, 1 H) | 1.45 | >68795 |
| P65 | H | Cl | 4,4,4-trifluorobutyl | CH₂C(O)NH₂ (with gem-dimethyl) | N | ¹H NMR (400 MHz, DMSO-d₆) δ ppm 1.90 (m, 2 H), 2.37 (dd, J = 16.3, 11.3 Hz, 2 H), 4.42 (t, J = 7.8 Hz, 2 H), 4.52 (s, 2 H), 5.47 (s, 2 H), 7.22 (d, J = 5.3 Hz, 1 H), 7.31 (m, 2 H), 7.69 (m, 2 H), 8.23 (d, J = 5.3 Hz, 1 H), 8.43 (s, 1 H) | 2.06 | >48603 |
| P66 | H | Cl | 4,4,4-trifluorobutyl | CH₂C(O)NHcyclopropyl | N | ¹H NMR (400 MHz, DMSO-d₆) δ ppm 0.44 (br. s., 2 H), 0.63 (d, J = 5.8 Hz, 2 H), 1.90 (m, 2 H), 2.37 (m, 2 H), 2.60-2.69 (m, 1 H), 4.42 (t, J = 7.0 Hz, 2 H), 4.50 (s, 2 H), 5.48 (s, 2 H), 7.21 (d, J = 5.0 Hz, 1 H), 7.31 (d, J = 8.8 Hz, 1 H), 7.69 (d, J = 4.3 Hz, 2 H), 8.23 (d, J = 5.0 Hz, 1 H), 8.35 (d, J = 2.8 Hz, 1 H), 8.43 (s, 1 H) | 1.995 | >55811 |
| P67 | H | Cl | 5-fluoropentyl | CH₂C(O)NHcyclopropyl | N | ¹H NMR (400 MHz, DMSO-d₆) δ ppm 0.37-0.49 (m, 2 H) 0.60-0.67 (m, 2 H) 1.63-1.71 (m, 1 H) 1.72-1.80 (m, 3 H) 2.65 (td, J = 7.28, 3.76 Hz, 1 H) 4.34-4.43 (m, 3 H) 4.53 (t, J = 5.27 Hz, 1 H) 4.57 (s, 2 H) 5.50 (s, 2 H) 7.30 (dd, J = 8.66, 1.88 Hz, 1 H) 7.43 (d, J = 5.77 Hz, 1 H) 7.62-7.70 (m, 2 H) 8.36 (d, J = 5.52 Hz, 1 H) 8.40 (d, J = 4.27 Hz, 1 H) 8.57 (s, 1 H) | 1.25 | 48249 |
| P68 | H | Cl | 5-fluoropentyl | CH₂C(O)OH | N | ¹H NMR (400 MHz, DMSO-d₆) δ ppm 1.58-1.79 (m, 4 H) 4.26 (s, 2 H) 4.32-4.42 (m, 3 H) 4.47-4.53 (m, 1 H) 5.44 (s, 2 H) 7.10 (d, J = 5.27 Hz, 1 H) 7.28 (dd, J = 8.53, 2.01 Hz, 1 H) 7.64 (d, J = 8.78 Hz, 1 H) 7.69 (d, J = 1.76 Hz, 1 H) 8.17 (d, J = 5.27 Hz, 1 H) 8.36 (s, 1 H) | 10 | >10299 |

TABLE 2-continued formula (I)

| | R₁ | R₂ | R₃ | R₄ | X—R₅ | ¹H NMR | WT activity EC₅₀ (nM) | SI CC₅₀/ EC50 |
|---|---|---|---|---|---|---|---|---|
| P69 | H | Cl | (CH₂)₄F | cyclopropyl | C—F | ¹H NMR (400 MHz, DMSO-d₆) δ ppm 0.76-0.95 (m, 2 H) 0.98-1.11 (m, 2 H) 1.53-1.80 (m, 4 H) 2.82-3.02 (m, 1 H) 4.32-4.42 (m, 3 H) 4.46-4.54 (m, 1 H) 5.29 (s, 2 H) 6.89 (m, J = 7.50, 2.50, 2.50 Hz, 1 H) 7.14 (dd, J = 8.78, 2.26 Hz, 1 H) 7.21 (dd, J = 8.53, 4.77 Hz, 1 H) 7.28 (dd, J = 8.53, 2.01 Hz, 1 H) 7.64 (d, J = 8.78 Hz, 1 H) 7.68 (d, J = 2.01 Hz, 1 H) | | |
| P70 | H | Cl | (CH₂)₃CN | cyclopropyl | CH | 1H NMR (400 MHz, DMSO-d6) δ ppm 0.87-0.94 (m, 2 H) 1.02-1.11 (m, 2 H) 2.00 (quin, J = 7.40 Hz, 2 H) 2.60 (t, J = 7.53 Hz, 2 H) 2.90-2.99 (m, 1 H) 4.41 (t, J = 7.53 Hz, 2 H) 5.35 (s, 2 H) 7.01-7.07 (m, 1 H) 7.07-7.13 (m, 1 H) 7.21 (d, J = 7.53 Hz, 1 H) 7.26 (d, J = 7.78 Hz, 1 H) 7.29 (dd, J = 8.66, 1.88 Hz, 1 H) 7.61-7.69 (m, 2 H) | 0.631 | >159787 |
| P71 | H | Cl | (CH₂)₄F | N,N-dimethyl carboxamide isobutyl | N | ¹H NMR (400 MHz, DMSO-d₆) δ ppm 1.60-1.79 (m, 4 H) 2.85 (s, 3 H) 3.10 (s, 3 H) 4.34-4.42 (m, 3 H) 4.51 (t, J = 5.40 Hz, 1 H) 4.85 (s, 2 H) 5.46 (s, 2 H) 7.21 (d, J = 5.27 Hz, 1 H) 7.29 (dd, J = 8.78, 2.01 Hz, 1 H) 7.65 (d, J = 8.78 Hz, 1 H) 7.69 (d, J = 1.76 Hz, 1 H) 8.21 (d, J = 5.27 Hz, 1 H) 8.42 (s, 1 H) | 2.5 | >39781 |
| P72 | H | Cl | (CH₂)₄F | N-cyclopropyl carboxamide isobutyl | N | ¹H NMR (400 MHz, DMSO-d₆) δ ppm 1.58-1.79 (m, 4 H) 2.62 (d, J = 4.52 Hz, 3 H) 4.31-4.42 (m, 3 H) 4.47-4.56 (m, 3 H) 5.45 (s, 2 H) 7.21 (d, J = 5.27 Hz, 1 H) 7.29 (dd, J = 8.66, 1.88 Hz, 1 H) 7.65 (d, J = 8.78 Hz, 1 H) 7.69 (d, J = 2.01 Hz, 1 H) 8.16 (d, J = 4.52 Hz, 1 H) 8.22 (d, J = 5.27 Hz, 1 H) 8.44 (s, 1 H) | 3.16 | >30931 |
| P73 | H | Cl | (CH₂)₃CN | cyclopropyl | C—F | 1H NMR (400 MHz, DMSO-d6) δ ppm 0.86-0.94 (m, 2 H) 1.01-1.09 (m, 2 H) 2.05 (quin, J = 7.40 Hz, 2 H) 2.62 (t, J = 7.40 Hz, 1 H) 2.89-3.00 (m, 1 H) 4.41 (t, J = 7.40 Hz, 2 H) 5.35 (s, 2 H) 6.88-6.97 (m, 1 H) 7.17 (dd, J = 9.03, 2.26 Hz, 1 H) 7.22 (dd, J = 8.53, 4.52 Hz, 1 H) 7.30 (dd, J = 8.66, 1.63 Hz, 1 H) 7.63-7.69 (m, 2 H) | 1.58 | 23633 |

TABLE 2-continued formula (I)

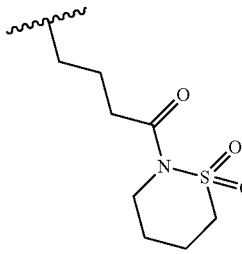

| | $R_1$ | $R_2$ | $R_3$ | $R_4$ | $X-R_5$ | $^1$H NMR | WT activity $EC_{50}$ (nM) | SI $CC_{50}/EC50$ |
|---|---|---|---|---|---|---|---|---|
| P74 | H | Br |  | 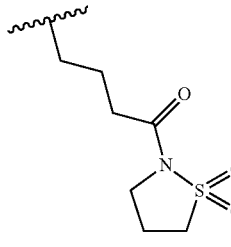 | N | $^1$H NMR (400 MHz, Chloroform-d) δ ppm 0.98-1.05 (m, 2 H) 1.13-1.20 (m, 2 H) 1.58-1.66 (m, 2 H) 1.97-2.07 (m, 2 H) 2.18-2.26 (m, 2 H) 2.87-2.97 (m, 3 H) 3.10 (t, J = 6.01 Hz, 2 H) 4.03 (t, J = 5.55 Hz, 2 H) 4.37 (t, J = 7.41 Hz, 2 H) 5.36 (s, 2 H) 7.15 (d, J = 5.12 Hz, 1 H) 7.31 (d, J = 8.65 Hz, 1 H) 7.38 (dd, J1 = 8.65 Hz, J2 = 1.74 Hz, 1 H) 7.83 (s, 1 H) 8.35 (d, J = 5.12 Hz, 1 H) 8.68 (s, 1 H) | 1.18 | >84529 |
| P75 | H | Br |  | 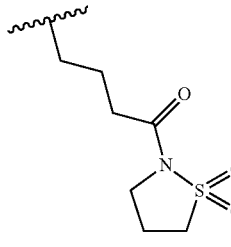 | N | $^1$H NMR (400 MHz, DMSO-d) δ ppm 0.85-0.92 (m, 2 H) 1.00-1.08 (m, 2 H) 1.89-1.98 (m, 2 H) 2.20-2.29 (m, 2 H) 2.71 (br, 2 H) 2.99 (q, J = 3.47 Hz, 1 H) 3.58 (br, 2 H) 3.73 (t, J = 6.53 Hz, 2 H) 4.35 (t, J = 7.50 Hz, 2 H) 5.39 (s, 2 H) 7.27 (d, J = 5.20 Hz, 1 H) 7.39 (dd, J1 = 8.68 Hz, J2 = 1.74 Hz, 1 H) 7.61 (d, J = 8.68 Hz, 1 H) 7.80 (d, J = 1.74 Hz, 1 H) 8.23 (d, J = 5.20 Hz, 1 H) 8.36 (s, 1 H) | 0.2 | >444590 |
| P76 | H | Br | 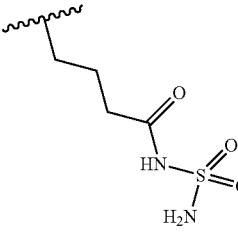 | 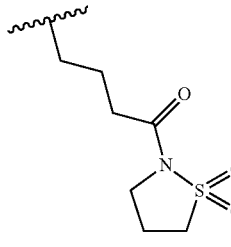 | N | $^1$H NMR (400 MHz, DMSO-d) δ ppm 0.88-0.94 (m, 2 H) 1.03-1.10 (m, 2 H) 1.82-1.92 (m, 2 H) 2.20-2.28 (m, 2 H) 2.97 (q, J = 3.47 Hz, 1 H) 4.34 (t, J = 7.98 Hz, 2 H) 5.42 (s, 2 H) 7.29 (d, J = 5.10 Hz, 1 H) 7.40 (dd, J1 = 8.68 Hz, J2 = 1.74 Hz, 1 H) 7.63 (d, J = 8.68 Hz, 1 H) 7.80 (d, J = 1.74 Hz, 1 H) 8.26 (d, J = 5.20 Hz, 1 H) 8.38 (s, 1 H) | 0.47 | >214887 |
| E. P77 | F. H | G. Br |  | 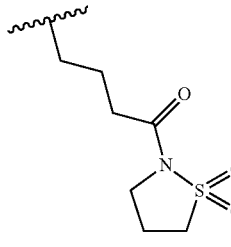 | N | $^1$H NMR (400 MHz, DMSO-d) δ ppm 0.88-0.94 (m, 2 H) 1.03-1.10 (m, 2 H) 1.84-1.94 (m, 2 H) 2.36 (t, J = 7.08 Hz, 2 H) 2.76 (s, 6 H) 2.99 (q, J = 3.47 Hz, 1 H) 4.34 (t, J = 7.45 Hz, 2 H) 5.41 (s, 2 H) 7.29 (d, J = 5.10 Hz, 1 H) 7.41 (dd, J1 = 8.68 Hz, J2 = 1.74 Hz, 1 H) 7.60 (d, J = 8.68 Hz, 1 H) 7.80 (d, J = 1.74 Hz, 1 H) 8.26 (d, J = 5.20 Hz, 1 H) 8.38 (s, 1 H) | 1.1 | >22961 |

TABLE 2-continued formula (I)

|  | R₁ | R₂ | R₃ | R₄ | X—R₅ | ¹H NMR | WT activity EC₅₀ (nM) | SI CC₅₀/EC50 |
|---|---|---|---|---|---|---|---|---|
| P78 | H | Br | (propylsulfonylamino-butanoyl chain) | cyclopropyl | N | ¹H NMR (400 MHz, DMSO-d) δ ppm 0.87-0.94 (m, 2 H) 0.96 (t, J = 7.31 Hz, 3 H) 1.03-1.10 (m, 2 H) 1.56-1.71 (m, 2 H) 1.82-1.94 (m, 2 H) 2.35 (t, J = 6.85 Hz, 2 H) 3.00 (q, J = 3.47 Hz, 1 H) 3.25 (t, H = 7.47, 2 H) 4.34 (t, J = 7.50 Hz, 2 H) 5.41 (s, 2 H) 7.29 (d, J = 5.20 Hz, 1 H) 7.39 (dd, J1 = 8.68 Hz, J2 = 1.74 Hz, 1 H) 7.63 (d, J = 8.68, 1 H) 7.80 (d, J = 1.74 Hz, 1 H) 8.26 (d, J = 5.20 Hz, 1 H) 8.39 (s, 1 H) 11.52-11.93 (br, 1 H) | 1.73 | >57893 |
| P79 | H | Br | (N-methyl methylsulfonylamino-butanoyl chain) | cyclopropyl | N | ¹H NMR (400 MHz, DMSO-d) δ ppm 0.85-0.91 (m, 2 H) 1.01-1.08 (m, 2 H) 1.86-1.96 (m, 2 H) 2.77 (d, J = 7.12 Hz, 2 H) 2.97 (q, J = 3.47 Hz, 1 H) 3.15 (s, 3 H) 3.31 (s, 3 H) 4.35 (t, J = 7.50 Hz, 2 H) 5.40 (s, 2 H) 7.27 (d, J = 5.10 Hz, 1 H) 7.40 (dd, J1 = 8.68 Hz, J2 = 1.74 Hz, 1 H) 7.60 (d, J = 8.68 Hz, 1 H) 7.78 (d, J = 1.74 Hz, 1 H) 8.24 (d, J = 5.20 Hz, 1 H) 8.38 (s, 1 H) | 0.56 | >177178 |
| P80 | H | Br | (methylsulfonylamino-butanoyl chain) | cyclopropyl | N | ¹H NMR (400 MHz, DMSO-d) δ ppm 0.88-0.95 (m, 2 H) 1.03-1.10 (m, 2 H) 1.80-1.90 (m, 2 H) 2.35 (d, J = 7.12 Hz, 2 H) 2.99 (q, J = 3.47 Hz, 1 H) 3.15 (s, 3 H) 4.35 (t, J = 7.50 Hz, 2 H) 5.41 (s, 2 H) 7.29 (d, J = 5.20 Hz, 1 H) 7.40 (dd, J1 = 8.68 Hz, J2 = 1.74 Hz, 1 H) 7.61 (d, J = 8.68, 1 H) 7.80 (d, J = 1.74 Hz, 1 H) 8.26 (d, J = 5.20 Hz, 1 H) 8.39 (s, 1H) 11.60-12.14 (br, 1 H) | 1 | >99444 |
| P81 | H | Br | (butylsulfonylamino-butanoyl chain) | cyclopropyl | N | ¹H NMR (400 MHz, DMSO-d) δ ppm 0.85 (t, J = 7.48 Hz, 3 H) 0.89-0.94 (m, 2 H) 1.03-1.10 (m, 2 H) 1.30-1.40 (m, 2 H) 1.53-1.62 (m, 2 H) 1.81-1.89 (m, 2 H) 2.27 (t, J = 6.85 Hz, 2 H) 3.00 (q, J = 3.47 Hz, 1 H) 3.16-3.22 (m, 2 H) 4.34 (t, J = 7.50 Hz, 2 H) 5.41 (s, 2 H) 7.29 (d, J = 5.20 Hz, 1 H) 7.39 (dd, J1 = 8.68 Hz, J2 = 1.74 Hz, 1 H) 7.63 (d, J = 8.68 Hz, 1 H) 7.79 (d, J = 1.74 Hz, 1 H) 8.24 (d, J = 5.20 Hz, 1 H) 8.38 (s, 1 H) 11.24-12.53 (br, 1 H) | 7.25 | >13798 |

TABLE 2-continued formula (I)

| | $R_1$ | $R_2$ | $R_3$ | $R_4$ | X—$R_5$ | $^1$H NMR | WT activity $EC_{50}$ (nM) | SI $CC_{50}$/$EC_{50}$ |
|---|---|---|---|---|---|---|---|---|
| P82 | H | Br | (CH2)3C(O)NH2 | cyclopropyl | N | $^1$H NMR (400 MHz, DMSO-d) δ ppm 0.89-0.94 (m, 2 H) 1.03-1.10 (m, 2 H) 1.80-1.90 (m, 2 H) 2.15 (t, J = 7.12 Hz, 3 H) 2.99 (q, J = 3.25 Hz, 1 H) 4.33 (t, J = 7.40 Hz, 2 H) 5.41 (s, 2 H) 6.83 (bs, 1 H) 7.30 (d, J = 5.40 Hz, 1 H) 7.34 (bs, 1 H) 7.40 (dd, J1 = 8.40 Hz, J2 = 200 Hz, 1 H) 7.61 (d, J = 8.40 Hz, 1 H) 7.80 (d, J = 2.00 Hz, 1 H) 8.26 (d, J = 5.3 Hz, 1 H) 8.38 (s, 1 H) | 0.58 | >85761 |
| P83 | H | Br | (CH2)3C(O)NHMe | cyclopropyl | N | $^1$H NMR (400 MHz, Chloroform-d) δ ppm 1.01-1.09 (m, 2 H) 1.17-1.24 (m, 2 H) 2.05-2.14 (m, 2 H) 2.20-2.27 (m, 2 H) 2.76 (d, J = 4.55 Hz, 3 H) 2.96-3.02 (m, 1 H) 4.37 (t, J = 6.82 Hz, 2 H) 5.38 (s, 2 H) 5.90 (bs, 1 H) 7.28-7.33 (m, 2 H) 7.38 (d, J = 8.77 Hz, 1 H) 7.82 (bs, 1 H) 8.39 (bs, 1 H) 8.70 (bs, 1 H) | 0.9 | >111709 |
| P84 | H | Cl | (CH2)4OH | CH2C(F)3... | N | $^1$H NMR (400 MHz, CHLOROFORM-d) δ ppm 1.56-1.67 (m, 2 H), 1.71-1.83 (m, 3 H), 3.67 (t, J = 6.02 Hz, 2 H), 4.27-4.35 (m, 2 H), 4.50 (q, J = 8.53 Hz, 2 H), 5.41 (s, 2 H), 7.01 (d, J = 5.52 Hz, 1 H), 7.23-7.29 (m, 2 H), 7.75 (t, J = 1.25 Hz, 1 H), (d, J = 5.27 Hz, 1 H), 8.77 (s, 1 H) | | |
| P85 | H | Cl | (CH2)4OH | CH2C(F)3... | C—F | $^1$H NMR (400 MHz, CHLOROFORM-d) δ ppm 1.58-1.68 (m, 2 H), 1.69-1.82 (m, 2 H), 1.89 (t, J = 5.5 Hz, 1 H), 3.66 (q, J = 5.8 Hz, 2 H), 4.25-4.37 (m, 2 H), 4.48 (q, J = 8.5 Hz, 2 H), 5.37 (s, 2 H), 6.84 (td, 7=9.0, 2.4 Hz, 1 H), 6.96 (dd, J = 8.5, 4.0 Hz, 1 H), 7.26 (s, 2 H), 7.37 (dd, J = 8.4, 2.4 Hz, 1 H), 7.78 (s, 1 H) | | |
| Ref1 | H | H | (CH2)3S(O)2Me | cyclopropyl | N | | 2.5 | >4315 |

TABLE 2-continued formula (I)

| | $R_1$ | $R_2$ | $R_3$ | $R_4$ | $X-R_5$ | $^1$H NMR | WT activity $EC_{50}$ (nM) | SI $CC_{50}/EC_{50}$ |
|---|---|---|---|---|---|---|---|---|
| Ref2 | H | H | (CH$_2$)$_4$OH chain | cyclopropyl | N | | 3.98 | >27750 |

TABLE 3 formula (I)

| | $R_1$ | $R_2$ | $R_3$ | $R_4$ | $X-R_5$ |
|---|---|---|---|---|---|
| P86 | H | Cl | -(CH$_2$)$_3$-C(O)-NH-S(O)$_2$-cyclopropyl | cyclopropyl | C—F |
| P87 | H | Cl | -(CH$_2$)$_3$-CN | -CH$_2$-C(CF$_3$)(F)- | C—F |
| P88 | H | Cl | -(CH$_2$)$_3$-CN | -CH$_2$-C(CF$_3$)(F)- | C—H |
| P89 | H | Cl | -(CH$_2$)$_3$-CN | -CH$_2$-C(CF$_3$)(F)- | N |

The invention claimed is:

1. A compound represented by formula I, a prodrug, N-oxide, addition salt, quaternary amine, metal complex, or a stereochemically isomeric form thereof;

formula (I)

wherein each X independently is C or N;

$R_1$ is H;

$R_2$ is selected from the group consisting of Br and Cl;

$R_3$ is —$(CR_6R_7)_n$—$R_8$;

$R_4$ is selected from the group consisting of H, $C_3$-$C_7$cycloalkyl, $C_2$-$C_{10}$ alkenyl, —$(CR_6R_7)_n$—$R_8$; —$CH_2$-p-Fluorophenyl, $CH_2CF_3$ and —$SO_2CH_3$;

$R_5$ is present where X is C, whereby each $R_5$ is selected, each independently, from the group consisting of H, $C_1$-$C_6$alkyl, $C_1$-$C_6$alkoxy, halogen, and CN;

$R_5$ is absent where X is N;

$R_6$ and $R_7$ are H;

$R_8$ is selected from the group consisting of H, OH, $CF_3$, $CHF_2$, F, Cl, $SO_2CH_3$, $SO_2C_3$-$C_7$cycloalkyl, $NR_6SO_2R_6$, $SO_2NR_6R_7$, $NR_6SO_2C_3$-$C_7$cycloalkyl, CN, $NR_6R_7$, COOH, $COOR_6$, $CONR_6R_7$, $OCOC_1$-$C_6$alkyl, $CONR_6SO_2R_7$, CONH—$R_6$—$SO_2R_7$, CONH—$R_6$—$SO_2NR_6R_7CONR_6SO_2NR_6R_7$, phtalimido or a 5 to 6 membered aliphatic or aromatic ring that optionally contains one or more heteroatoms selected from the group N, S, O;

n is an integer having a value from 1 to 6.

2. A compound according to claim 1 wherein $R_4$ is selected from the group consisting of H, $C_3$-$C_7$cycloalkyl, $C_2$-$C_{10}$ alkenyl, and —$SO_2CH_3$;

$R_8$ is selected from the group consisting of H, OH, $CF_3$, $CHF_2$, F, $SO_2CH_3$, $SO_2C_3$-$C_7$cycloalkyl, $NR_6SO_2R_6$, $SO_2NR_6R_7$, $NR_6SO_2C_3$-$C_7$cycloalkyl, CN, $NR_6R_7$.

3. A compound according to claim 1 wherein $R_2$ is Br.

4. A compound according to claim 1 wherein $R_2$ is Cl.

5. A compound according to claim 1, wherein n is 2-4.

6. A compound according to claim 1, wherein $R_8$ is selected from the group consisting of F, CN, OH, $CF_3$ and $SO_2CH_3$.

7. A compound according to claim 1, wherein $R_8$ is selected from the group consisting of F, CN, OH, and $SO_2CH_3$.

8. A compound according to claim 1, wherein $R_4$ is $C_3$-$C_7$cycloalkyl or $CH_2CF_3$.

9. A compound according to claim 1, wherein $R_4$ is cyclopropyl or $CH_2CF_3$.

10. A compound according to claim 1, wherein one X is N and the other X's are C.

11. A compound according to claim 10, wherein the N is in para position to N—$R_4$.

12. A compound according to claim 1, wherein at most one $R_5$ is selected from the group consisting of $C_1$-$C_6$alkyl, $C_1$-$C_6$alkoxy, halogen, and CN.

13. A compound according to claim 1, wherein all $R_5$ are H.

14. A compound according to claim 1, wherein $R_2$ is Cl; one X is N and the other X's are C, wherein the N is in para position to N—$R_4$; and $R_4$ is cyclopropyl or $CH_2CF_3$.

15. A pharmaceutical composition comprising a pharmaceutically acceptable carrier, and as active ingredient a therapeutically effective amount of a compound as claimed in claim 1.

16. A process for preparing a pharmaceutical composition as claimed in claim 15, said process comprising intimately mixing a pharmaceutically acceptable carrier with a therapeutically effective amount of compound.

* * * * *